(12) United States Patent
Kim et al.

(10) Patent No.: US 10,927,215 B2
(45) Date of Patent: Feb. 23, 2021

(54) POLYMERIZABLE COMPOSITION

(71) Applicant: LG Chem, Ltd., Seoul (KR)

(72) Inventors: Sang Woo Kim, Daejeon (KR); Seung Hee Lee, Daejeon (KR); Ki Ho Ahn, Daejeon (KR)

(73) Assignee: LG Chem, Ltd.

( * ) Notice: Subject to any disclaimer, the term of this patent is extended or adjusted under 35 U.S.C. 154(b) by 21 days.

(21) Appl. No.: 16/324,417

(22) PCT Filed: Aug. 8, 2016

(86) PCT No.: PCT/KR2016/008695
§ 371 (c)(1),
(2) Date: Feb. 8, 2019

(87) PCT Pub. No.: WO2018/030552
PCT Pub. Date: Feb. 15, 2018

(65) Prior Publication Data
US 2019/0169364 A1    Jun. 6, 2019

(51) Int. Cl.
| | |
|---|---|
| *C08G 63/44* | (2006.01) |
| *C08K 7/02* | (2006.01) |
| *C08K 3/04* | (2006.01) |
| *C08K 3/00* | (2018.01) |
| *C08G 65/40* | (2006.01) |
| *C08G 73/06* | (2006.01) |
| *C08G 73/14* | (2006.01) |
| *C07D 487/04* | (2006.01) |
| *C07D 209/50* | (2006.01) |

(52) U.S. Cl.
CPC ............. *C08G 63/44* (2013.01); *C08G 65/40* (2013.01); *C08G 73/065* (2013.01); *C08G 73/0644* (2013.01); *C08G 73/14* (2013.01); *C08K 3/00* (2013.01); *C08K 3/04* (2013.01); *C08K 3/046* (2017.05); *C08K 7/02* (2013.01); *C07D 209/50* (2013.01); *C07D 487/04* (2013.01)

(58) Field of Classification Search
CPC .................................................... C08G 73/14
See application file for complete search history.

(56) References Cited

U.S. PATENT DOCUMENTS

| | | | |
|---|---|---|---|
| 4,244,857 A | 1/1981 | Serafini et al. | |
| 4,408,035 A | 10/1983 | Keller | |
| 4,587,325 A * | 5/1986 | Keller ................... | C08G 73/00 252/500 |
| 4,619,986 A * | 10/1986 | Keller ................... | C07C 255/00 528/362 |
| 4,816,533 A * | 3/1989 | McLean ................ | C08G 59/10 525/526 |
| 5,003,039 A | 3/1991 | Keller | |
| 5,003,078 A | 3/1991 | Keller | |
| 5,004,801 A | 4/1991 | Keller et al. | |
| 5,132,396 A | 7/1992 | Keller | |
| 5,139,054 A | 8/1992 | Long et al. | |
| 5,159,054 A * | 10/1992 | Keller ................... | C07D 209/48 528/125 |
| 5,208,318 A | 5/1993 | Keller | |
| 5,237,045 A | 8/1993 | Burchill et al. | |
| 5,292,854 A | 3/1994 | Keller | |
| 5,350,828 A | 9/1994 | Keller et al. | |
| 5,939,508 A * | 8/1999 | Keller ................... | C08G 59/32 525/481 |
| 5,965,268 A | 10/1999 | Sastri et al. | |
| 6,001,926 A | 12/1999 | Sastri et al. | |
| 6,297,298 B1 * | 10/2001 | Keller ................... | C08G 73/00 522/6 |
| 2014/0058057 A1 * | 2/2014 | Das ...................... | C08G 73/1067 528/208 |
| 2015/0267022 A1 * | 9/2015 | Hu ........................ | B32B 18/00 442/1 |
| 2016/0168327 A1 * | 6/2016 | Keller ................... | C08K 5/42 524/710 |
| 2016/0311976 A1 * | 10/2016 | Laskoski ................ | C07C 45/64 |
| 2018/0118666 A1 * | 5/2018 | Lee ....................... | C07C 255/54 |
| 2018/0346646 A1 * | 12/2018 | Kim ...................... | C08G 73/1007 |
| 2018/0355180 A1 * | 12/2018 | Ahn ...................... | C08L 79/00 |
| 2019/0127525 A1 * | 5/2019 | Lee ....................... | C08G 73/06 |
| 2019/0276605 A1 * | 9/2019 | Ahn ...................... | C08G 75/12 |
| 2020/0080610 A1 * | 3/2020 | Kim ...................... | C08L 33/18 |

(Continued)

FOREIGN PATENT DOCUMENTS

| | | | |
|---|---|---|---|
| EP | 3385302 A1 | 10/2018 | |
| JP | S48031297 A | 4/1973 | |
| JP | H01103632 A | 4/1989 | |

(Continued)

OTHER PUBLICATIONS

International Search Report for PCT/KR2016/008695, dated May 1, 2017.
Ji, S., et al., "A novel curing agent for phthalonitrile monomers: Curing behaviors and properties of the polymer network." Polymer, Electronic publication date Janury 7, 2016, vol. 84, pp. 365-370.
Sharma, P., et al., "Curing and Thermal Behaviour of Epoxy Resin in the Presence of a Mixture of Imide-Amines." Journal of Thermal Analysis and Calorimetry, vol. 94, Issue 3, Received: Dec. 26, 2007; Accepted: Jan. 28, 2008, pp. 805-815.

(Continued)

*Primary Examiner* — Liam J Heincer

(74) *Attorney, Agent, or Firm* — Lerner, David, Littenberg, Krumholz & Mentlik, LLP

(57) ABSTRACT

A polymerizable composition, a prepolymer, a phthalonitrile resin, or a composite provided herein has excellent heat resistance and does not cause defects that may adversely affect physical properties. In addition, the polymerizable composition exhibits appropriate curing properties, processing temperatures and process windows and to be capable of forming a composite of excellent physical properties.

16 Claims, 11 Drawing Sheets

(56) References Cited

U.S. PATENT DOCUMENTS

2020/0087592 A1* 3/2020 Kim .................. C08G 73/026

FOREIGN PATENT DOCUMENTS

| JP | 2001519255 | A | 10/2001 |
| JP | 200670096 | A | 3/2006 |
| JP | 2016023285 | A | 2/2016 |
| KR | 20010030872 | A | 4/2001 |
| KR | 20010072625 | A | 7/2001 |
| KR | 100558158 | B1 | 3/2006 |
| KR | 20160059444 | A | 5/2016 |
| KR | 20160115543 | A | 10/2016 |

OTHER PUBLICATIONS

Extended European Search Report including the Written Opinion for Application No. EP 16912751.1 dated Jul. 4, 2019.

* cited by examiner

POLYMERIZABLE COMPOSITION

CROSS-REFERENCE TO RELATED APPLICATION

The present application is a national phase entry under 35 U.S.C. § 371 of International Application No. PCT/KR2016/008695, filed on Aug. 8, 2016, the disclosure of which is incorporated herein by reference.

TECHNICAL FIELD

The present application relates to a polymerizable composition, a prepolymer, a phthalonitrile resin, a composite, a process for preparing the same, and a use thereof.

BACKGROUND ART

The phthalonitrile resin can be used in various applications. For example, a composite formed by impregnating a filler such as glass fiber or carbon fiber with the phthalonitrile resin can be used as a material for automobiles, airplanes, ships, and the like. The process for producing the composite may include, for example, a process of mixing a mixture of phthalonitrile and a curing agent or a prepolymer formed by reaction of the mixture with a filler and then curing the mixture (see, for example, Patent Document 1).

When the curing agent is decomposed in the course of the reaction of the phthalonitrile compound with the curing agent, defects such as survival of voids occur in the prepolymer, resin or composite and such defects may be factors that hinder the physical properties of the final product. Therefore, in order to solve the above problem, a method of controlling the ratio of the curing agent to a low level or adjusting the temperature to a low level upon the curing reaction may be considered, but such a method may deteriorate the curing efficiency and may also adversely affect the physical properties of the final product.

(Patent Document 1) Korean Patent No. 0558158

DISCLOSURE

Technical Problem

The present application provides a polymerizable composition, a prepolymer, a resin, a composite, a process for preparing the same, and a use thereof. It is one object of the present application to provide a polymerizable composition comprising a curing agent which has excellent heat resistance and does not cause defects such as voids that may adversely affect physical properties. In addition, it is another object of the present application that the polymerizable composition exhibits appropriate curing properties, processing temperatures and process windows and is capable of forming a composite of excellent physical properties.

Technical Solution

The present application relates to a polymerizable composition. In one example, the polymerizable composition may be a composition capable of forming a so-called phthalonitrile resin through a polymerization reaction.

The polymerizable composition may comprise a phthalonitrile compound and a curing agent.

The kind of the phthalonitrile compound usable in the polymerizable composition is not particularly limited, and for example, a compound comprising 2 or more, 2 to 20, 2 to 16, 2 to 12, 2 to 8, or 2 to 4 phthalonitrile structures which are capable of forming a phthalonitrile resin through reaction with a curing agent, can be used. There are various compounds known to be suitable for forming the phthalonitrile resin, and in the present application, all of the above known compounds can be used. In one example, as examples of the compounds, those known in U.S. Pat. Nos. 4,408,035, 5,003,039, 5,003,078, 5,004,801, 5,132,396, 5,139,054, 5,208,318, 5,237,045, 5,292,854 or U.S. Pat. No. 5,350,828 can be exemplified, and various compounds known in the art, besides those mentioned by above documents, can be included in the examples.

The polymerizable composition may further comprise a curing agent, and as the curing agent, a compound represented by Formula 1 below may be used. The curing agent of the following formula has an imide structure in the molecular structure, thereby exhibiting excellent heat resistance, and may form a polymerizable composition which does not generate voids or the like that may adversely affect physical properties, even when an excess amount of the curing agent is contained in the polymerizable composition or the polymerizable composition is processed or cured at a high temperature.

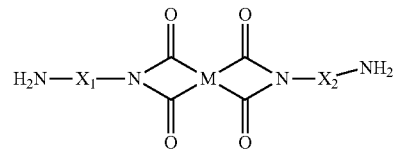

[Formula 1]

In Formula 1, M is a tetravalent radical, $X_1$ and $X_2$ are each independently an alkylene group, an alkylidene group or an aromatic divalent radical.

In the present application, the term n-valent radical (where n is any number) may mean a tetravalent residue derived from a predetermined compound, unless otherwise specified. For example, in Formula 1 above, M may be a tetravalent radical derived from an aliphatic, alicyclic or aromatic compound. In this case, for example, the M may have a structure in which radicals formed by leaving four hydrogen atoms from the aliphatic, alicyclic or aromatic compound are linked with carbon atoms of carbonyl groups of Formula 1, respectively.

Here, as the aliphatic compound, linear or branched alkane, alkene or alkyne may be exemplified. As the aliphatic compound, an alkane, alkene or alkyne having 2 to 20 carbon atoms, 2 to 16 carbon atoms, 2 to 12 carbon atoms, 2 to 8 carbon atoms or 2 to 4 carbon atoms may be used. In this case, the alkane, alkene or alkyne may be optionally substituted by one or more substituents.

Here, as the alicyclic compound, a hydrocarbon compound comprising a non-aromatic ring structure having 3 to 20 carbon atoms, 3 to 16 carbon atoms, 3 to 12 carbon atoms, 3 to 8 carbon atoms, or 3 to 4 carbon atoms may be exemplified. Such an alicyclic hydrocarbon compound may also contain at least one heteroatom such as oxygen or nitrogen as a ring constituent atom, and may optionally be substituted with one or more substituents, if necessary.

In addition, the aromatic compound in the above may be exemplified by benzene, a benzene-containing compound or a derivative of any one of the foregoing. Here, the benzene-containing compound may mean a compound having a structure in which two or more benzene rings are condensed while sharing one or two carbon atoms or directly linked or a structure in which they are linked by an appropriate linker. The aromatic compound may comprise, for example, 6 to 25, 6 to 20 or 6 to 12 carbon atoms, and may be substituted by one or more substituents, if necessary.

In one example, the alicyclic or aromatic compound forming the tetravalent radical may be exemplified by a compound represented by any one of Formulas 2 to 7 below.

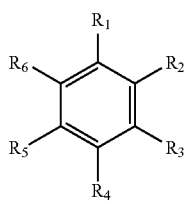

[Formula 2]

In Formula 2 above, $R_1$ to $R_6$ are each independently hydrogen, an alkyl group, an alkoxy group or an aryl group.

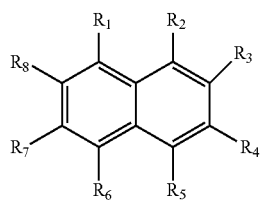

[Formula 3]

In Formula 3, $R_1$ to $R_8$ are each independently hydrogen, an alkyl group, an alkoxy group or an aryl group.

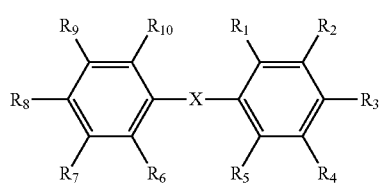

[Formula 4]

In Formula 4, $R_1$ to $R_{10}$ are each independently hydrogen, an alkyl group, an alkoxy group or an aryl group, X is a single bond, an alkylene group, an alkylidene group, an oxygen atom, a sulfur atom, a carbonyl group, $-A_1-O-C(=O)-A_2-$, $-A_1-C(=O)-O-A_2-$, $-S(=O)-$ or $-S(=O)_2-$. Here, $A_1$ and $A_2$ may be each independently a single bond or an alkylene group.

In this specification, the term single bond means the case where no separate atom is present at the corresponding site, and for example, when X is a single bond in Formula 4, it means the case where no separate atom is present at that part, and in this case, benzene rings on both sides of X may be directly connected to form a biphenyl structure.

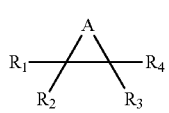

[Formula 5]

In Formula 5, $R_1$ to $R_4$ are each independently hydrogen, an alkyl group or an alkoxy group, and A is an alkylene group or an alkenylene group.

In Formula 5, two of $R_1$ to $R_4$ may be also linked to each other to form an alkylene group, and the alkylene group or alkenylene group of A may contain one or more oxygen atoms as a hetero atom.

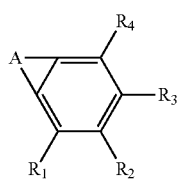

[Formula 6]

In Formula 6, $R_1$ to $R_4$ are each independently hydrogen, an alkyl group or an alkoxy group, and A is an alkylene group.

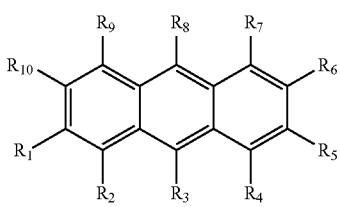

[Formula 7]

In Formula 7, $R_1$ to $R_{10}$ are each independently hydrogen, an alkyl group or an alkoxy group.

In the present application, the term alkyl group may be an alkyl group having 1 to 20 carbon atoms, 1 to 16 carbon atoms, 1 to 12 carbon atoms, 1 to 8 carbon atoms or 1 to 4 carbon atoms, unless otherwise specified. The alkyl group may be linear, branched or cyclic and, if necessary, may be substituted by one or more substituents.

In the present application, the term alkoxy group may be an alkoxy group having 1 to 20 carbon atoms, 1 to 16 carbon atoms, 1 to 12 carbon atoms, 1 to 8 carbon atoms or 1 to 4 carbon atoms, unless otherwise specified. The alkoxy group may be linear, branched or cyclic, and, if necessary, may be substituted by one or more substituents.

In the present application, the term aryl group may mean a monovalent residue derived from the above-described aromatic compound, unless otherwise specified. In the present application, the category of the term aryl group may include not only the functional group commonly referred to as an aryl group but also a so-called aralkyl group or arylalkyl group.

In the present application, the term alkylene group or alkylidene group may mean an alkylene group or an alkylidene group, having 1 to 20 carbon atoms, 1 to 16 carbon atoms, 1 to 12 carbon atoms, 1 to 8 carbon atoms or 1 to 4 carbon atoms, unless otherwise specified. The alkylene group or alkylidene group may be linear, branched or cyclic. In addition, the alkylene or alkylidene group may be optionally substituted with one or more substituents.

As the substituent optionally substituted in the aliphatic compound, alicyclic compound, aromatic compound, alkyl group, alkoxy group, aryl group, alkylene group or alkylidene group, and the like in the present application, halogen such as chlorine or fluorine, an epoxy group such as a glycidyl group, an epoxyalkyl group, a glycidoxyalkyl group or an alicyclicepoxy group, a acryloyl group, a methacryloyl group, an isocyanate group, a thiol group, an alkyl group, an alkoxy group or an aryl group, and the like may be exemplified, without being limited thereto.

Here, as the compound of Formula 2, benzene, alkylbenzene or dialkylbenzene and the like may be exemplified, without being limited thereto.

In addition, as the compound of Formula 4, biphenyl or a compound represented by any one of Formulas A to F may be exemplified, without being limited thereto.

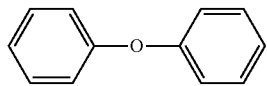

[Formula A]

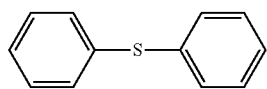

[Formula B]

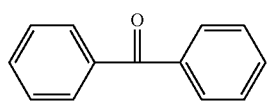

[Formula C]

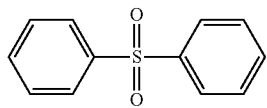

[Formula D]

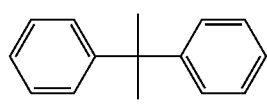

[Formula E]

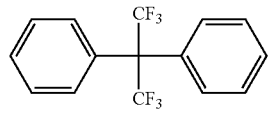

[Formula F]

As the compound of Formula 5, for example, a cycloalkane having 4 to 8 carbon atoms such as cyclohexane, or a cyclohexene which may be substituted with at least one alkyl group, and the like, or a compound represented by any one of Formulas G to I may be exemplified, without being limited thereto.

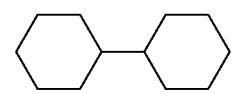

[Formula G]

[Formula H]

[Formula I]

Here, as the compound of Formula 6, a compound represented by Formula J, which may be substituted with one or more alkyl groups, may be exemplified, without being limited thereto.

[Formula J]

For example, radicals are formed by leaving four hydrogen atoms from the above compounds, and the radicals may be included in the structure of Formula 1.

These radicals may be formed by direct elimination of the substituents $R_1$ to $R_{10}$ of Formulas 2 to 7 above, or also formed by leaving hydrogen atoms belonging to an alkyl group, alkoxy group, aryl group, alkylene group or alkenylene group which is a substituent capable of being present in $R_1$ to $R_{10}$.

For example, when the radicals are derived from the compound of Formula 2, one or more, two or more, three or more, or four of $R_1$ to $R_6$ of Formula 2 may form radicals, or the radicals may be formed by leaving hydrogen atoms of the alkyl group, alkoxy group or aryl group present in the $R_1$ to $R_6$. Here, the formation of radicals may mean that the moieties are linked to carbon atoms of carbonyl groups of Formula 1, as described above. For example, in Formula 2 above, when $R_2$, $R_3$, $R_5$ and $R_6$ form radicals linked to Formula 1, a core structure such as the compound CA1 in Examples to be described below may be formed.

In one example, the tetravalent radical of Formula 1 may be a tetravalent radical derived from the compound represented by any one of Formulas 2 to 4 above. In this case, although $R_1$ to $R_6$ of Formula 2, $R_1$ to $R_8$ of Formula 3 or $R_1$ to $R_{11}$ of Formula 4 are each independently hydrogen, an alkyl group, an alkoxy group, or an aryl group, four or more of each formula may form radicals linked to Formula 1. Here, each of those forming no radical may be hydrogen, an alkyl group or an alkoxy group, or hydrogen or an alkyl group. In one example, $R_2$, $R_3$, $R_5$ and $R_6$ in Formula 2 may form the radicals, and $R_1$ and $R_4$ may be each independently hydrogen, an alkyl group, an alkoxy group or an aryl group, or hydrogen, an alkyl group or an alkoxy group, or hydrogen or an alkyl group. Also, $R_3$, $R_4$, $R_8$ and $R_7$ in Formula 3 may form the radicals, and $R_1$, $R_2$, $R_5$ and $R_6$ may be each independently hydrogen, an alkyl group, an alkoxy group or an aryl group, or hydrogen, an alkyl group or an alkoxy group, or hydrogen or an alkyl group. Also, $R_2$, $R_3$, $R_8$ and $R_9$ in Formula 4 may form the radicals, and $R_1$, $R_4$, $R_5$, $R_6$, $R_7$ and $R_{10}$ may be each independently hydrogen, an alkyl group, an alkoxy group or an aryl group, or hydrogen, an alkyl group or an alkoxy group, or hydrogen or an alkyl group.

In Formula 4, X may be an alkylene group, an alkylidene group, an oxygen atom or a sulfur atom. In another example, X in Formula 4 may be an alkylene group, an alkylidene group or an oxygen atom.

In Formula 1, $X_1$ and $X_2$ are each independently an alkylene group, an alkylidene group or an aromatic divalent radical, and in another example, they may be the same or different aromatic divalent radicals. In another example, the aromatic divalent radical may be a divalent radical derived from an aromatic compound having 6 to 40 carbon atoms. Here, the aromatic divalent radical may be a divalent radical derived from the above-mentioned aromatic compound.

In one example, $X_1$ and $X_2$ of Formula 1 above may be each independently a divalent radical derived from a compound represented by any one of Formulas 8 to 10 below.

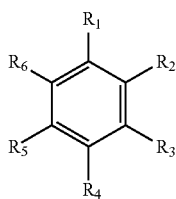

[Formula 8]

In Formula 8, $R_1$ to $R_6$ are each independently hydrogen, an alkyl group, an alkoxy group, an aryl group, a hydroxy group or a carboxyl group.

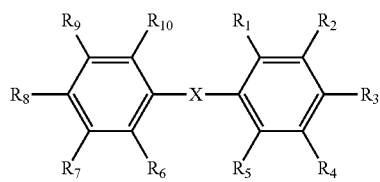

[Formula 9]

In Formula 9, $R_1$ to $R_{10}$ are each independently hydrogen, an alkyl group, an alkoxy group, a hydroxy group, a carboxyl group or an aryl group and X is a single bond, an alkylene group, an alkylidene group, an oxygen atom, a sulfur atom, a carbonyl group, $-NR_{11}-$, $-S(=O)-$ or $-S(=O)_2-$, where $R_{11}$ is hydrogen, an alkyl group, an alkoxy group or an aryl group.

Here, the meaning of the single bond is as defined in Formula 4.

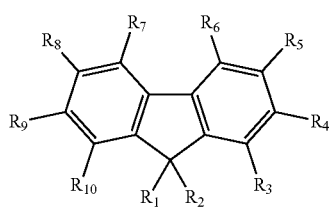

[Formula 10]

In Formula 10, $R_1$ to $R_{10}$ are each independently hydrogen, an alkyl group, an alkoxy group, a hydroxy group, a carboxyl group or an aryl group.

As the compound of Formula 8, benzene which may be substituted with at least one hydroxyl group or carboxyl group may be exemplified, without being limited thereto.

In addition, as the compound of Formula 9, biphenyl which may be substituted with at least one hydroxy group or carboxyl group or a compound which is represented by any one of Formulas A to F above or a compound which is represented by any one of Formulas A to F above and may be substituted with at least one hydroxyl group or a carboxyl group or a compound which is represented by Formulas K to N below or a compound which is represented by Formulas K to N below and may be substituted with at least one hydroxy group or carboxyl group may be exemplified, without being limited thereto.

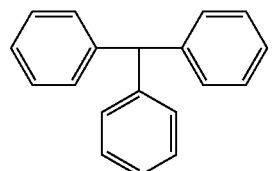

[Formula K]

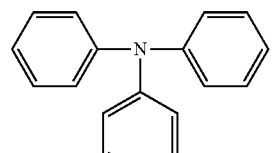

[Formula L]

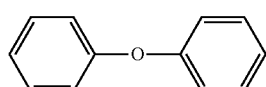

[Formula M]

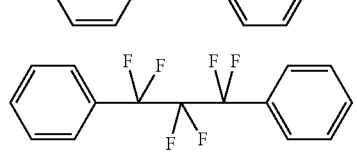

[Formula N]

As the compound of Formula 10, a compound which is represented by Formula 0 below or a compound which is represented by Formula 0 below and may be substituted with at least one hydroxy group or carboxyl group may be exemplified, without being limited thereto.

[Formula O]

In one example, the aromatic divalent radical may be a radical derived from the compound of Formula 8 above, and an example thereof may include phenylene, but is not limited thereto. When the divalent radical is phenylene, the substitution position of one amine group may be ortho, meta or para position based on the moiety linked to N in $X_1$ of Formula 1, and the substitution position of one amine group may be also ortho, meta or para position based on the moiety linked to N in $X_2$ of Formula 1.

The compound of Formula 1 can be synthesized according to synthesis methods of known organic compounds, and the specific method thereof is not particularly limited. For example, the compound of Formula 1 can be formed by dehydration and condensation reactions of a dianhydride compound and a diamine compound, and the like.

The compound of Formula 1 has a high boiling point and is not volatilized or decomposed at a high temperature, thereby forming no void capable of adversely affecting physical properties of the composite in processing or curing processes, while stably maintaining the curing property of the polymerizable composition. Accordingly, in one example, the compound may have a decomposition temperature of 300° C. or higher, 350° C. or higher, 400° C. or higher, or 500° C. or higher. In the present application, the term decomposition temperature may mean a temperature at which the decomposition rate of the compound of Formula 1 is maintained in the range of 10 wt % or less, 5 wt % or less, or 1 wt % or less. The upper limit of the decomposition temperature is not particularly limited and may be, for example, about 1,000° C. or less.

The compound of the Formula 1 can easily adjust the process window of the reactant or the polymerizable composition itself, that is, the difference between the melting temperature and the curing temperature of the polymerizable composition or the prepolymer formed therefrom, by selecting M of the core or $X_1$ or $X_2$ as the linker, and thus can act as a curing agent having various physical properties depending on applications.

The ratio of the curing agent in the polymerizable composition is not particularly limited. The above ratio can be adjusted so that the desired curability can be ensured in consideration of, for example, the ratio or kind of the curable component such as the phthalonitrile compound contained in the composition. For example, the curing agent may be included in about 0.02 to 1.5 moles per mole of the phthalonitrile compound contained in the polymerizable composition. However, the above ratio is only an example of the present application. Usually, the process window tends to become narrow if the ratio of the curing agent in the polymerizable composition is high, while the curing property tends to become insufficient if the ratio of the curing agent is low, so that the suitable ratio of the curing agent can be selected in consideration of these points, and the like.

The polymerizable composition of the present application exhibits proper curing property, melting temperature and process window through using the compound of Formula 1, and it is possible to provide a polymerizable composition and a prepolymer capable of forming a composite having excellent physical properties without deterioration of physical properties due to voids, and the like.

Thus, in one example, the processing temperature of the polymerizable composition may be in the range of 150° C. to 350° C. In the present application, the term processing temperature may mean a temperature at which the compound, the following polymerizable composition or prepolymer containing it, etc. is present in a processable state. Such a processing temperature may be, for example, a melting temperature (Tm) or a glass transition temperature (Tg). In this case, the process window of the polymerizable composition, that is, the absolute value of the difference (Tc−Tp) between the processing temperature (Tp) and the curing temperature (Tc) of the phthalonitrile compound and the compound of Formula 1, may be 30° C. or higher, 50° C. or higher, or 100° C. or higher. In one example, the curing temperature (Tc) may be higher than the processing temperature (Tp). Such a range may be advantageous, for example, for securing proper processability in the process of producing a composite to be described below by using a polymerizable composition. The upper limit of the process window is not particularly limited, but for example, the absolute value of the difference (Tc−Tp) between the processing temperature (Tp) and the curing temperature (Tc) may be 400° C. or lower or 300° C. or lower.

The polymerizable composition may further comprise various additives. As an example of such an additive, various fillers may be exemplified. The kind of the material that can be used as the filler is not particularly limited, and any known filler suitable for the intended use may be used. Exemplary fillers may be exemplified by a metal material, a ceramic material, glass, a metal oxide, a metal nitride or a carbon-based material, but are not limited thereto. In addition, the form of the filler is also not particularly limited and may be various forms, such as fibrous materials such as aramid fibers, glass fibers or ceramic fibers, or woven fabrics, nonwoven fabrics, cords or strings, formed by the material, particles containing nanoparticles, polygons or other amorphous forms. As an example of the carbon-based material, graphite, graphene, or carbon nanotubes, and the like, or derivatives or isomers such as their oxides, and the like may be exemplified. However, the component which may be further contained in the polymerizable composition may include various monomers known to be applicable to the production of so-called engineering plastics such as polyimide, polyamide, polystyrene and the like, or other additives without limitation depending on the purpose.

The present application also relates to a prepolymer formed by the reaction of the polymerizable composition, that is, the polymerizable composition comprising the phthalonitrile compound and the compound of Formula 1.

In the present application, the term prepolymer state may mean a state in which the reaction of the phthalonitrile compound with the compound of the Formula 1 occurs in the polymerizable composition to some extent (for example, a stage in which the polymerization of a so-called A or B stage step occurs), or a state which does not reach the fully polymerized state and exhibits appropriate fluidity, and thus, for example, is possible to process the composite, as described below. In one example, the prepolymer state may mean a state in which the polymerization of the polymerizable composition proceeds to some extent and for which a melt viscosity measured at any one temperature in the range of about 150° C. to 250° C. is 100 cP to 10,000 cP, 100 cP to 5,000 cP or 100 cP to 3000 cP.

The prepolymer may also exhibit excellent curing property, a low melting temperature and a wide process window.

For example, the processing temperature of the prepolymer may be in the range of 150° C. to 350° C. In this case, the process window of the prepolymer, that is, the absolute value of the difference (Tc−Tp) between the processing temperature (Tp) and the curing temperature (Tc) may be 30° C. or higher, 50° C. or higher, or 100° C. or higher. In one example, the curing temperature (Tc) may be higher than the processing temperature (Tp). Such a range may be advantageous, for example, for securing proper processability in the process of producing a composite to be described below by using a polymerizable composition. The upper limit of the process window is not particularly limited, but for example, the absolute value of the difference (Tc−Tp) between the processing temperature (Tp) and the curing temperature (Tc) may be 400° C. or lower or 300° C. or lower.

The prepolymer may further comprise any known additives in addition to the above components. As an example of such an additive, the above-mentioned fillers and the like may be exemplified, without being limited thereto.

The present application also relates to a phthalonitrile resin which is a polymer of said polymerizable composition. Such a resin can be formed, for example, by polymerizing the above-described polymerizable composition or prepolymer.

The present application also relates to a composite. The composite may comprise the above-described phthalonitrile resin and the filler. As described above, if the polymerizable composition of the present application is used, it is possible to achieve appropriate curing property, melt temperature and process window, and to prevent voids and the like that can adversely affect the physical properties even at high temperatures applied in the process of forming the composite or the resin, whereby a so-called reinforced polymer composite having excellent physical properties can be easily formed. The composite thus formed may comprise the phthalonitrile resin and the filler, and may be applied to various applications including durables for automobiles, airplanes, ships, and the like.

The kind of the filler is not particularly limited and may be suitably selected in consideration of the intended use. As the usable filler, fibrous materials such as carbon fibers, aramid fibers, glass fibers or ceramic fibers, or woven fabrics, non-woven fabrics, cords or strings, formed by the material, or carbon nanomaterials such as carbon nanotubes or graphene, and the like may be exemplified, without being limited thereto.

The ratio of the filler is not particularly limited, and may be set in an appropriate range according to the intended use.

The present application also relates to a precursor for preparing the composite, wherein the precursor may comprise, for example, the polymerizable composition described above and the filler, or the prepolymer described above and the filler.

The composite can be prepared in a known manner using the precursor. For example, the composite can be formed by curing the precursor.

In one example, the precursor may be prepared by blending the polymerizable composition or the prepolymer, which is prepared by compounding a phthalonitrile compound with the compound of Formula 1 in a molten state, with the filler in a state molten by heating or the like. For example, the above-described composite may be prepared by molding the precursor produced as above into a desired shape and then curing it. A method of forming a prepolymer or the like in the above process, a process for preparing a composite by compounding such a prepolymer and the like with a filler, and processing and curing it may be carried out according to a known method.

Advantageous Effects

The present application can provide a polymerizable composition comprising a curing agent which has excellent heat resistance and does not cause defects such as voids that may adversely affect physical properties. In addition, the present application allows for the polymerizable composition to exhibit appropriate curing properties, processing temperatures and process windows and to be capable of forming a composite of excellent physical properties.

MODE FOR INVENTION

Hereinafter, the polymerizable composition or the like of the present application will be specifically described by way of Examples and Comparative Examples, but the scope of the polymerizable composition and the like is not limited to the following Examples.

1. TGA (Thermogravimetric Analysis)

The TGA analysis was performed using a TGA e850 instrument from Mettler-Toledo. The analysis was performed in an $N_2$ flow atmosphere with increasing the temperature for the sample from about 25° C. to 800° C. at a rate of 10° C./min.

2. FT-IR (Fourier-Transform Infrared Spectroscopy)

The FT-IR analysis was performed by ATR (Attenuated Total Reflectance) method using the equipment from Varian. As a sample, a prepolymer of Examples or Comparative Examples was thermally cured, pulverized and powdered, and then measured, where the FT-IR peaks were measured as an absorption wavelength over wavelengths of 400 $cm^{-1}$ to 4000 $cm^{-1}$.

Production Example 1. Synthesis of Compound (PN1)

Figure 1:
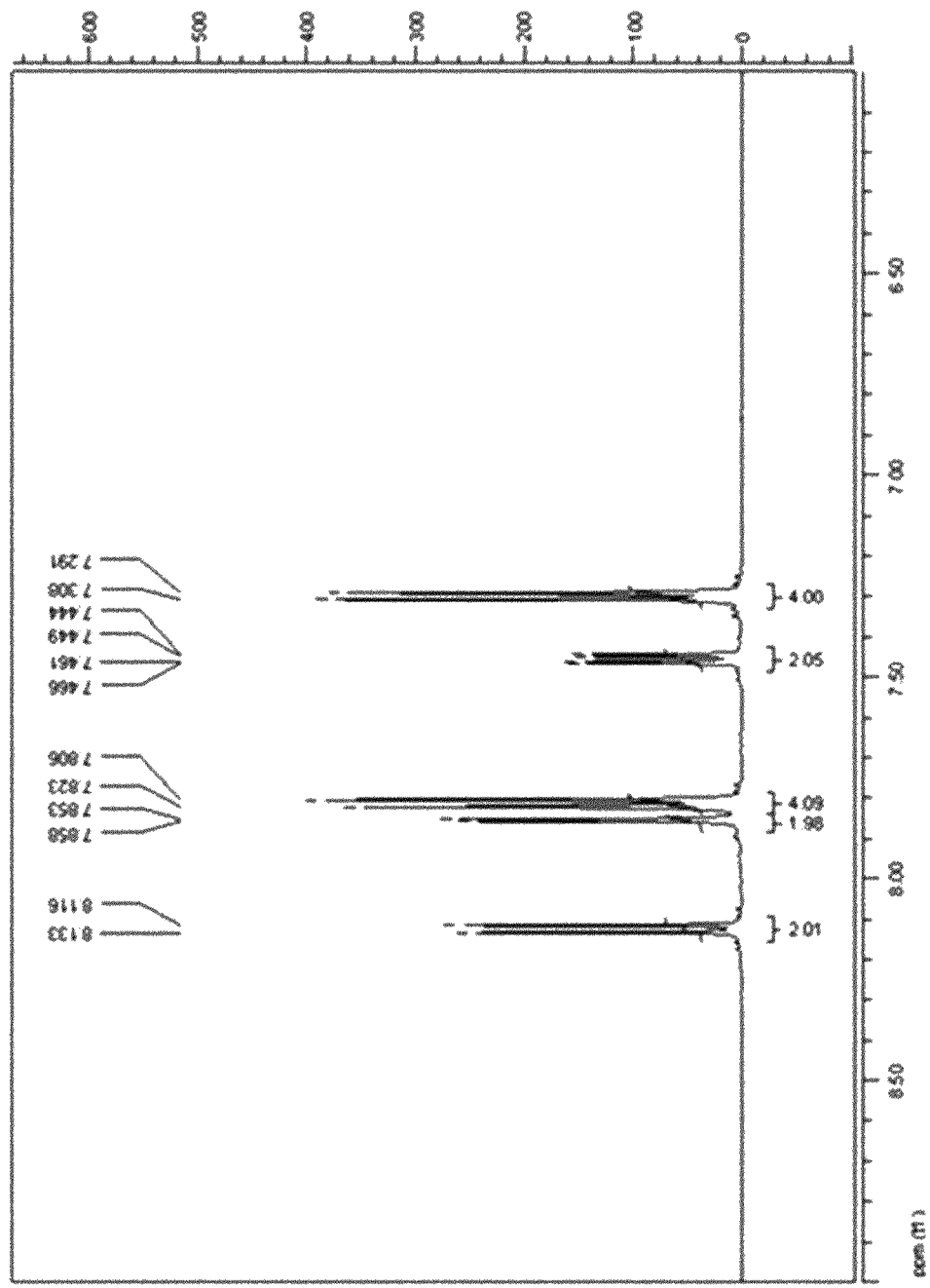
FIGS. 1 to 10 are the NMR analysis results for compounds prepared in Production Examples.

The compound of Formula I below was synthesized in the following manner. 27.9 g of the compound of Formula II below and 100 g of DMF (Dimethyl Formamide) were added to a 3 neck RBF (3 neck round bottom flask) and dissolved by stirring at room temperature. Subsequently, 51.9 g of the compound of Formula III below was further added, and 50 g of DMF was added thereto, followed by dissolving with stirring. Subsequently, 62.2 g of potassium carbonate and 50 g of DMF were added together, and the temperature was raised to 85° C. with stirring. After reacting in the above state for about 5 hours, the reactant was cooled to room temperature. The cooled reaction solution was poured into a 0.2N hydrochloric acid aqueous solution, neutralized and precipitated, followed by filtering and then washing with water. The filtered reactant was then dried in a vacuum oven at 100° C. for 1 day, and after removal of water and the residual solvent, the compound of Formula I below was obtained in a yield of about 83% by weight. The NMR result for the compound of Formula I was shown in FIG. 1.

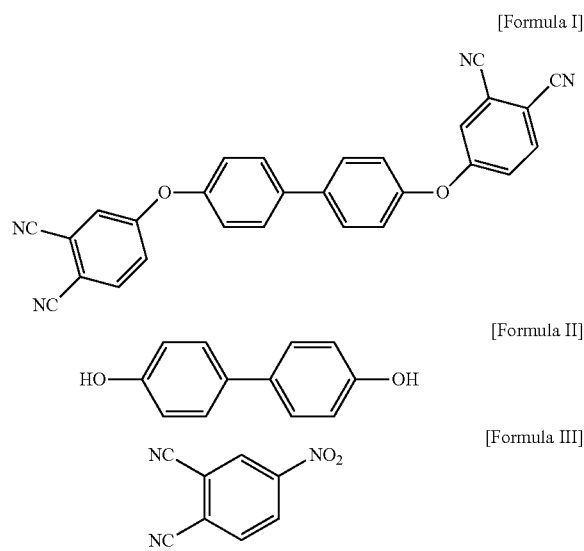

Production Example 2. Synthesis of Compound (PN2)

Figure 2:
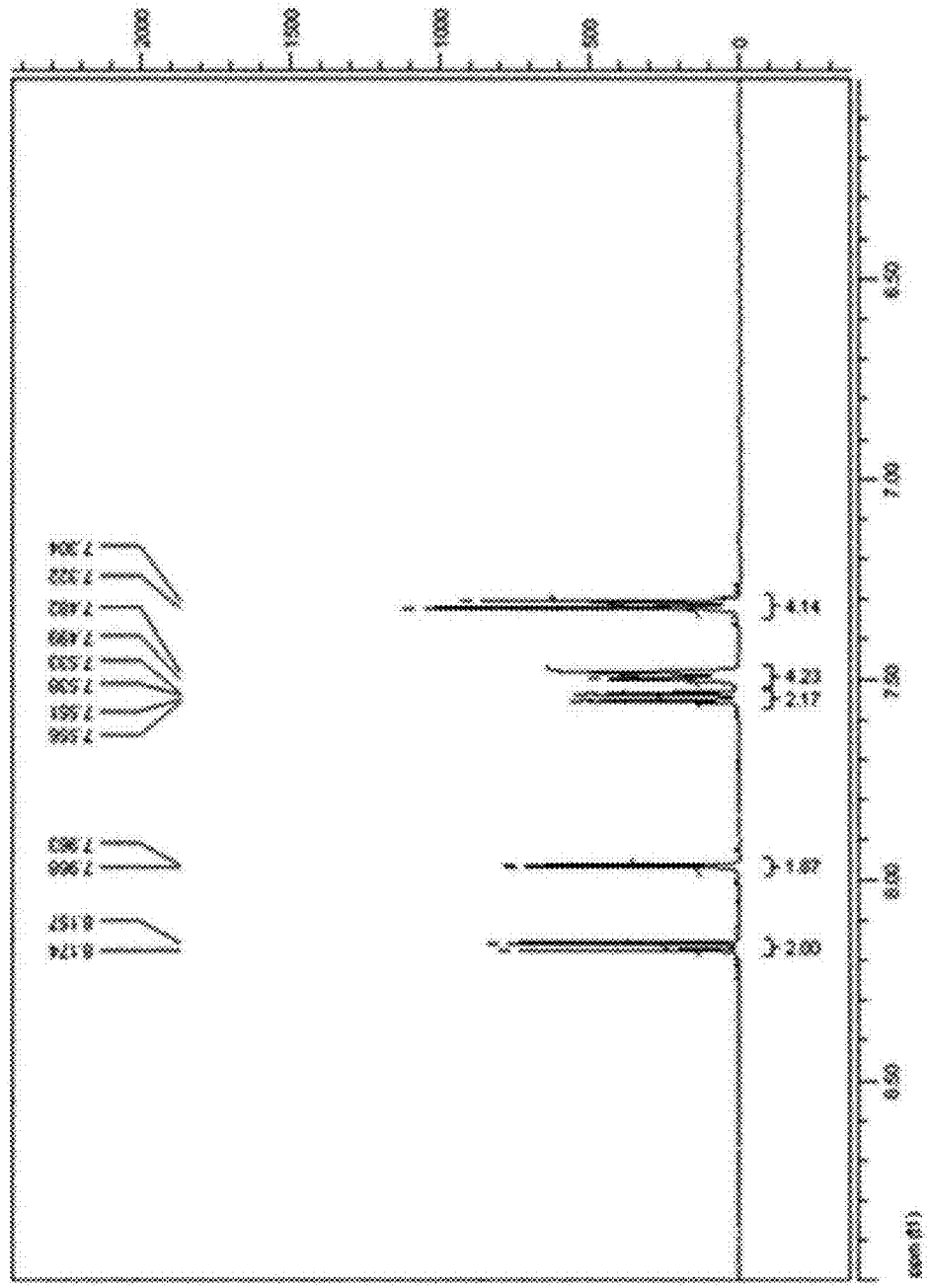

50.4 g of the compound of Formula IV below and 150 g of DMF (Dimethyl Formamide) were added to a 3 neck RBF (3 neck round bottom flask) and dissolved by stirring at room temperature. Then, 51.9 g of the compound of Formula III in Production Example 1 was further added, and 50 g of DMF was added thereto, followed by dissolving with stirring. Subsequently, 62.2 g of potassium carbonate and 50 g of DMF were added together, and the temperature was raised to 85° C. with stirring. After reacting in the above state for about 5 hours, the reactant was cooled to room temperature. The cooled reaction solution was poured into a 0.2N hydrochloric acid aqueous solution, neutralized and precipitated, followed by filtering and then washing with water. The filtered reactant was then dried in a vacuum oven at 100° C. for 1 day, and after removal of water and the residual solvent, the compound of Formula V below (PN2) was obtained in a yield of about 87% by weight. The NMR result for the compound of Formula V was shown in FIG. 2.

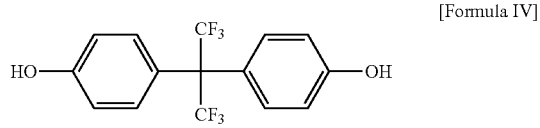

Figure 3:
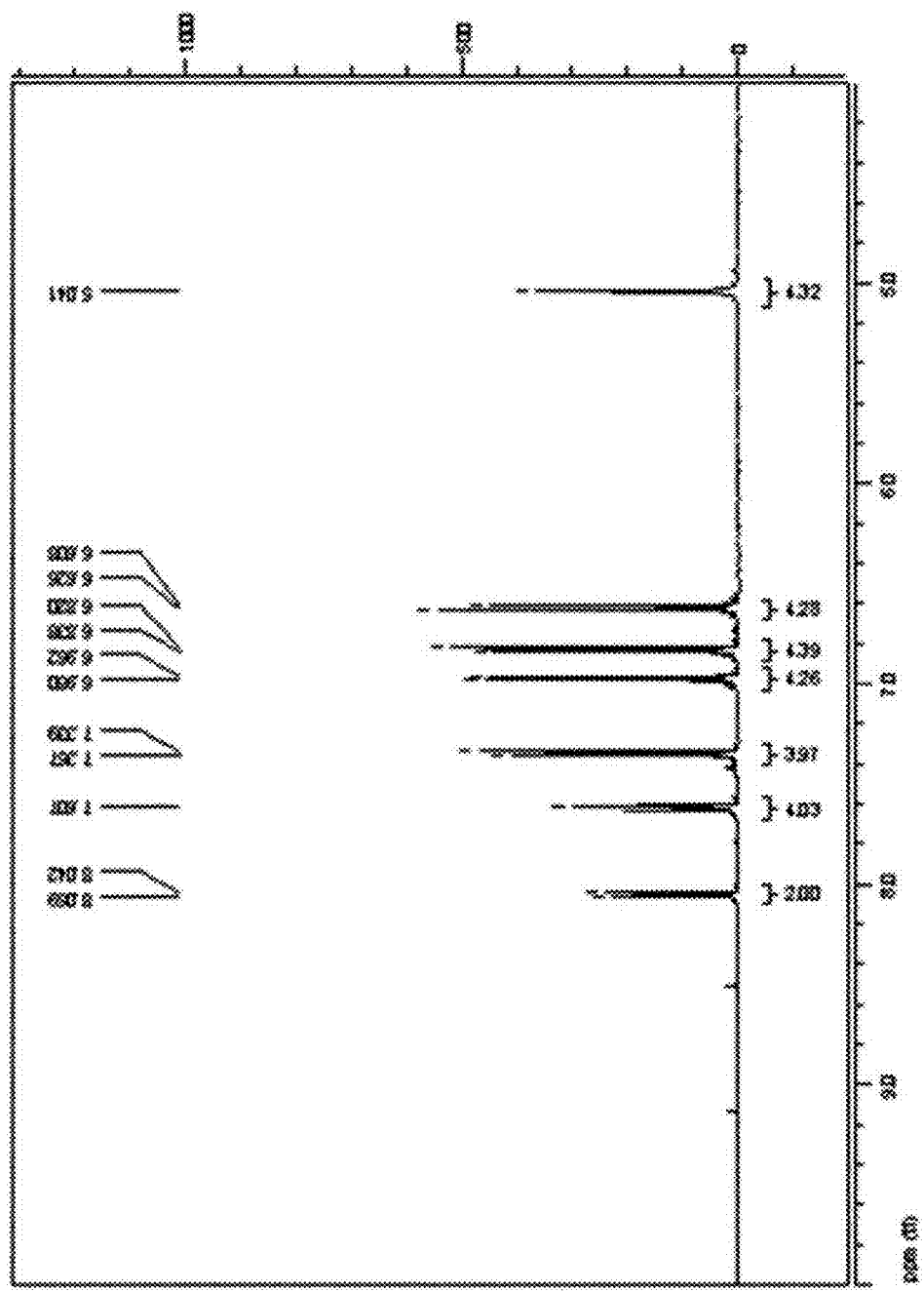

[Formula IV]

charged into a 3 neck RBF (3 neck round bottom flask) and dissolved by stirring at room temperature. The above solution was cooled with a water bath, and 12.4 g of the compound of Formula VII below was slowly divided into three times and added thereto together with 45 g of NMP. When all the added compounds were dissolved, 18 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to extraction with methanol to remove the residual reactant and dried in a vacuum oven to obtain the compound of Formula IIX in a yield of about 81% by weight. The NMR analysis result of the compound of Formula IIX was shown in FIG. 3.

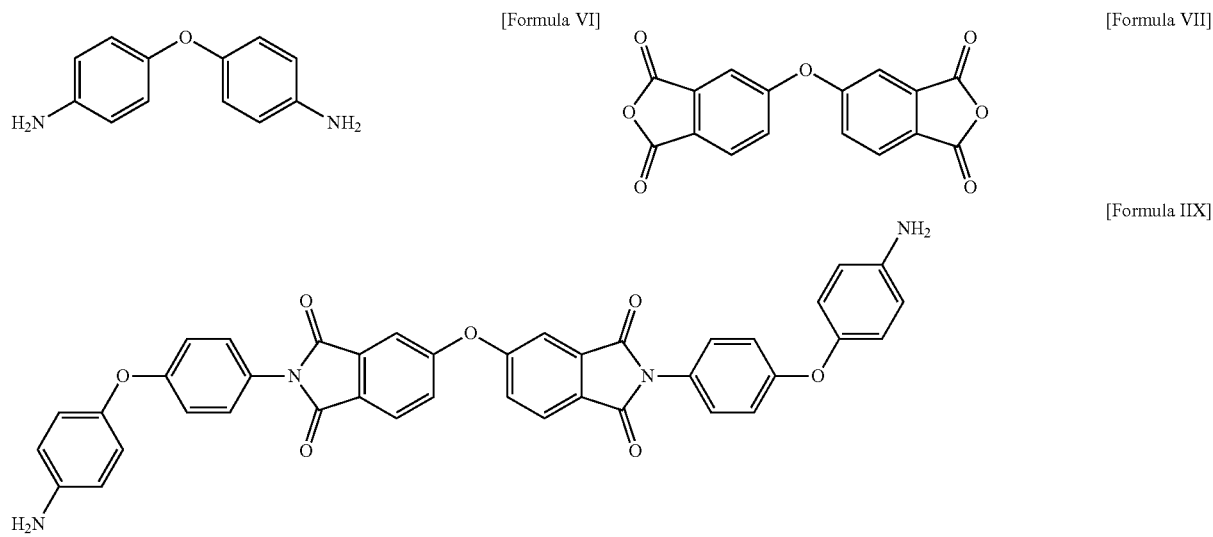 [SMILES: Nc1ccc(Oc2ccc(N)cc2)cc1 ; O=C1OC(=O)c2cc(Oc3ccc4c(c3)C(=O)OC4=O)ccc21 ; Nc1ccc(Oc2ccc(N3C(=O)c4ccc(Oc5ccc6c(c5)C(=O)N(c5ccc(Oc7ccc(N)cc7)cc5)C6=O)cc4C3=O)cc2)cc1]

[Formula VI]

[Formula VII]

[Formula IIX]

-continued

[Formula V]

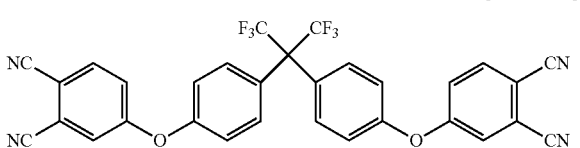

Production Example 3. Synthesis of Compound (CA1)

The compound of Formula IIX below was synthesized in the following manner. First, 24 g of the compound of Formula VI and 45 g of NMP (N-methyl-pyrrolidone) were Production Example 4. Synthesis of Compound (CA2)

Figure 4:
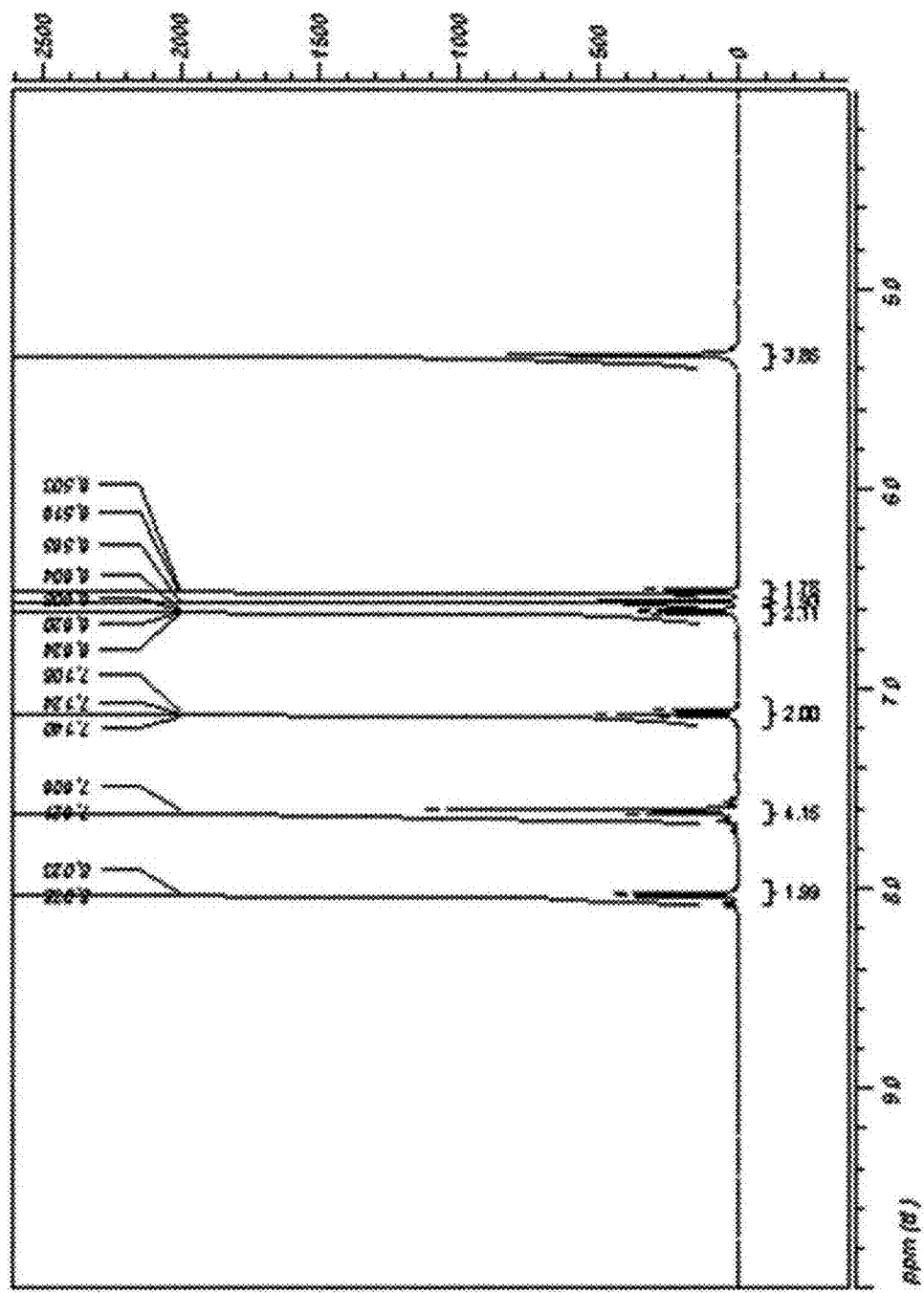
Figure 5:
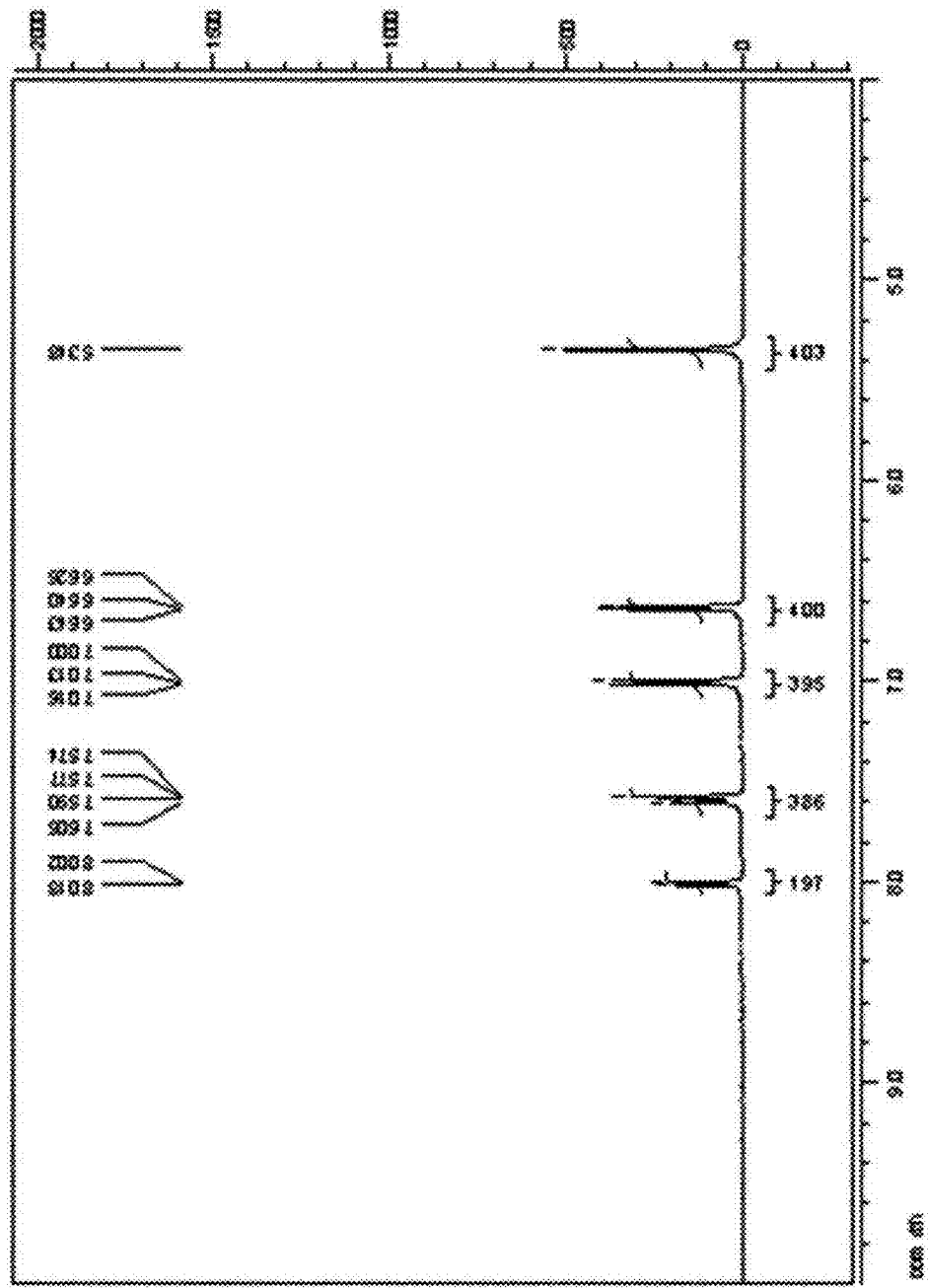

The compound of Formula X below was synthesized in the following manner. First, 13 g of the compound of Formula IX below and 33 g of NMP (N-methyl-pyrrolidone) were charged into a 3 neck RBF (3 neck round bottom flask) and dissolved by stirring at room temperature. The above solution was cooled with a water bath, and 12.4 g of the compound of Formula VII in Production Example 3 was slowly divided into three times and added thereto together with 30 g of NMP. When all the added compounds were dissolved, 13 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to extraction with methanol to remove the residual reactant and dried in a vacuum oven to obtain the compound of Formula X in a yield of about 78% by weight. The NMR analysis result of the compound of Formula X was shown in FIG. 4.

reactant and dried in a vacuum oven to obtain the compound of Formula XII in a yield of about 80% by weight. The NMR analysis result of the compound of Formula XII was shown in FIG. 5.

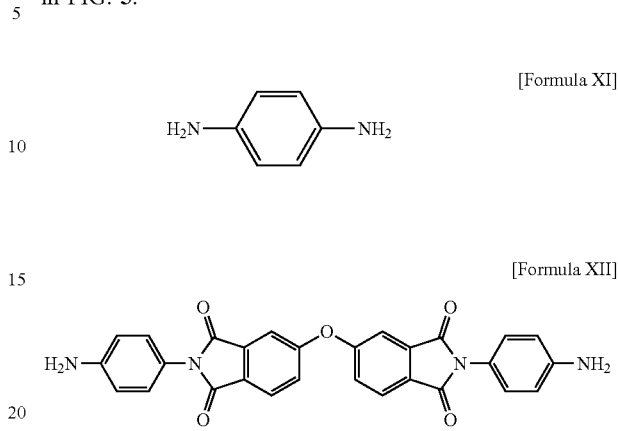

[Formula XI]

[Formula XII]

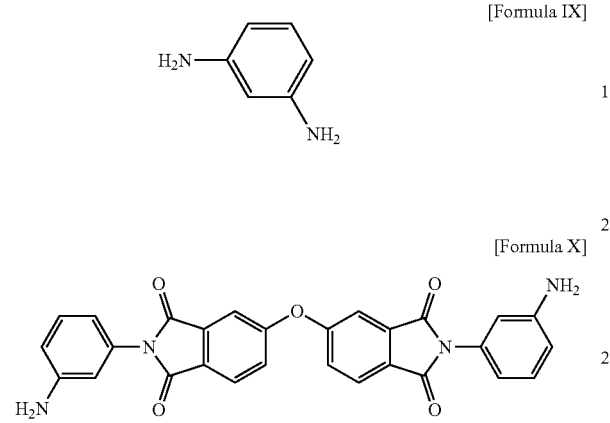

[Formula IX]

[Formula X]

Production Example 5. Synthesis of Compound (CA3)

The compound of Formula XII below was synthesized in the following manner. First, 13 g of the compound of Formula XI below and 33 g of NMP (N-methyl-pyrrolidone) were charged into a 3 neck RBF (3 neck round bottom flask) and dissolved by stirring at room temperature. The above solution was cooled with a water bath, and 12.4 g of the compound of Formula VII in Production Example 3 was slowly divided into three times and added thereto together with 30 g of NMP. When all the added compounds were dissolved, 13 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to extraction with methanol to remove the residual

Production Example 6. Synthesis of Compound (CA4)

Figure 6:
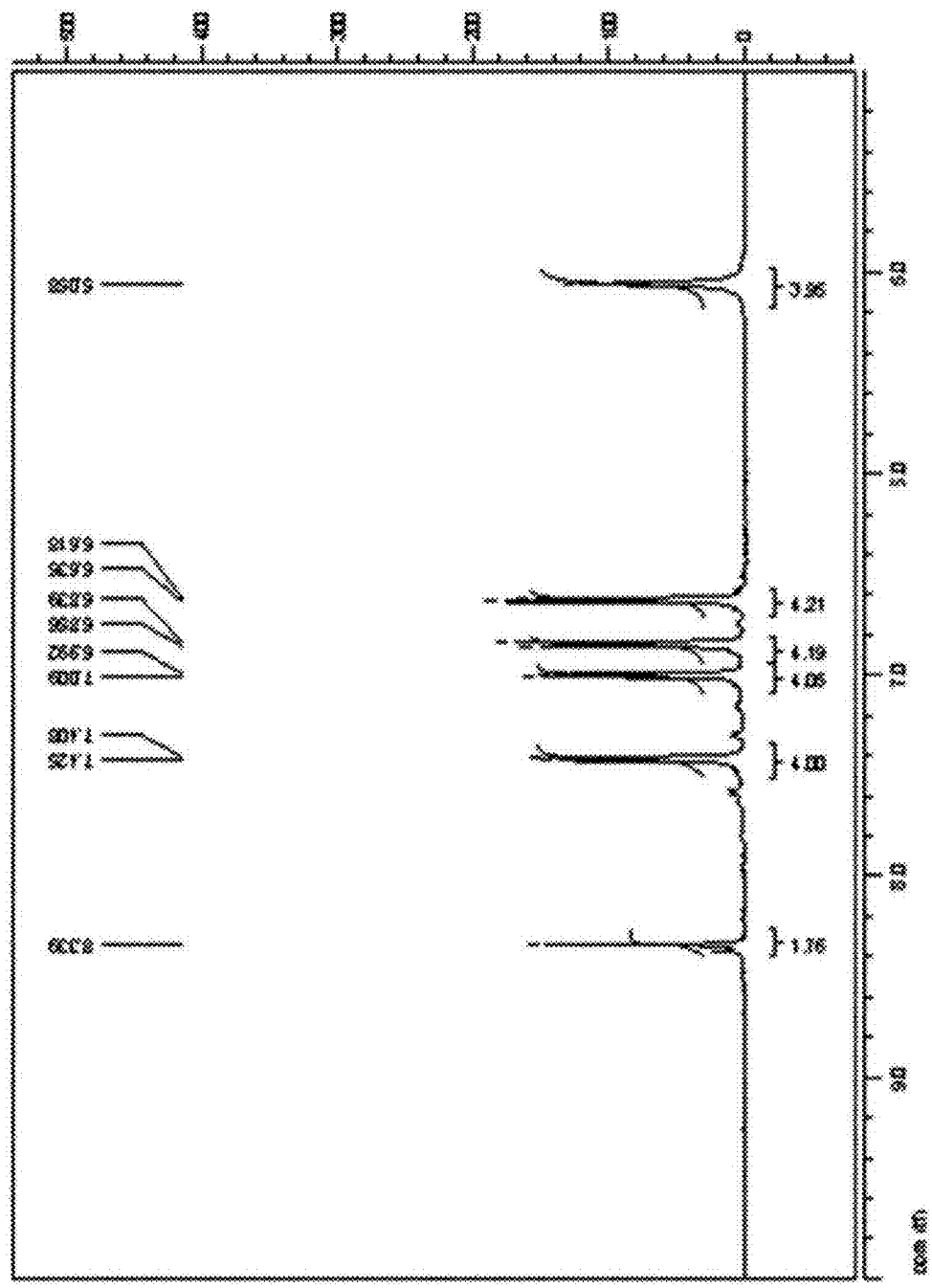

The compound of Formula 14 below was synthesized by dehydration and condensation of a diamine and a dianhydride. 24 g of the compound of Formula VI (4,4'-oxydianiline) in Production Example 3 and 40 g of NMP (N-methylpyrrolidone) were charged into a 3 neck RBF (3 neck round bottom flask) and dissolved by stirring at room temperature. The above solution was cooled with a water bath, and 8.7 g of the compound of Formula 13 below was slowly divided into three times and added thereto together with 40 g of NMP. When all the added compounds were dissolved, 16 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to extraction with methanol to remove the residual reactant and dried in a vacuum oven to obtain the compound of Formula 14 in a yield of about 85% by weight. The NMR analysis result of the compound of Formula 14 was shown in FIG. 6.

[Formula 13]

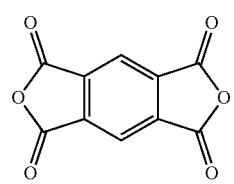

-continued

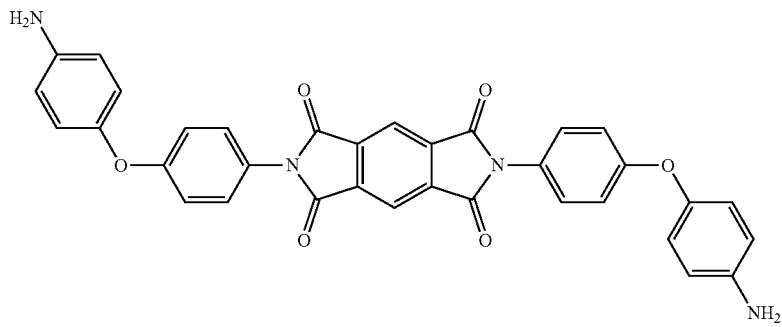

[Formula 14]

Production Example 7. Synthesis of Compound (CA5)

Figure 7:
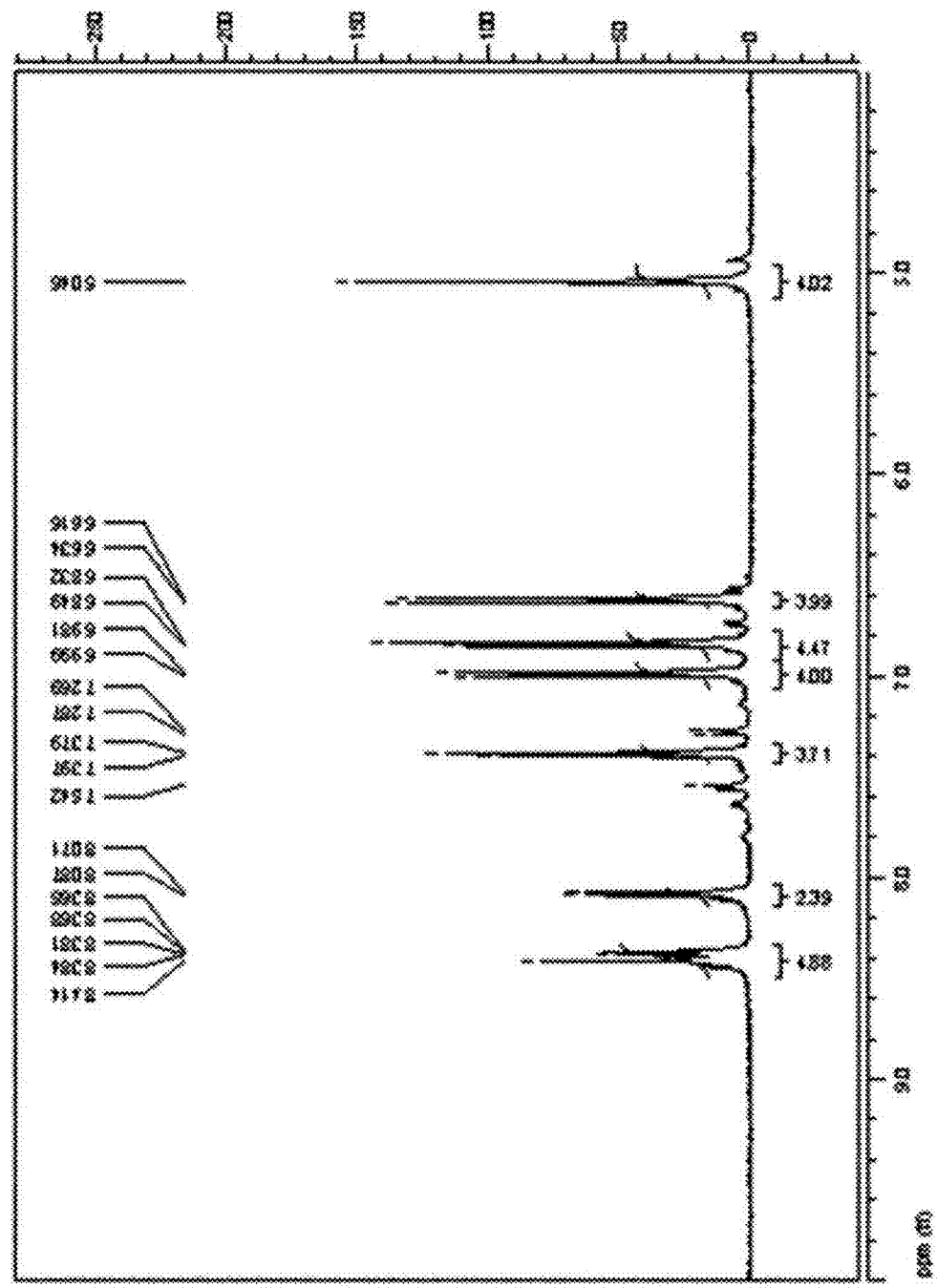

The compound of Formula 16 below was synthesized by dehydration and condensation of a diamine and a dianhydride. 24 g of the compound of Formula VI (4,4'-oxydianiline) in Production Example 3 and 45 g of NMP (N-methylpyrrolidone) were charged into a 3 neck RBF (3 neck round bottom flask) and dissolved by stirring at room temperature. The above solution was cooled with a water bath, and 11.8 g of the compound of Formula 15 below was slowly divided into three times and added thereto together with 45 g of NMP. When all the added compounds were dissolved, 18 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to soxhlet extraction with methanol to remove the residual reactant and dried in a vacuum oven to obtain the compound of Formula 16 in a yield of about 77% by weight. The NMR analysis result of the compound of Formula 16 was shown in FIG. 7.

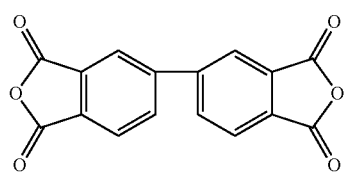

[Formula 15]

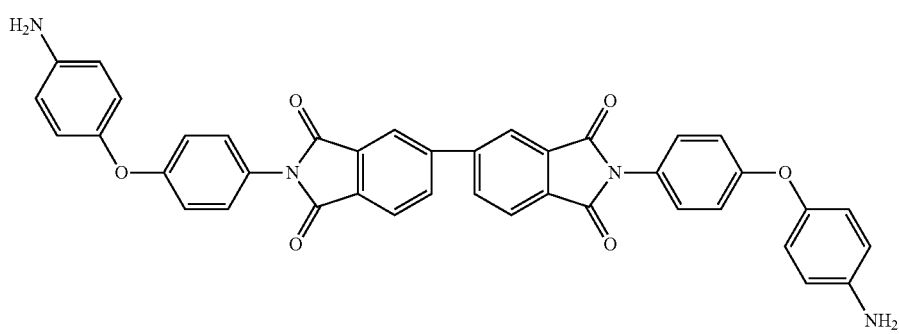

[Formula 16]

Production Example 8. Synthesis of Compound (CA6)

Figure 8:
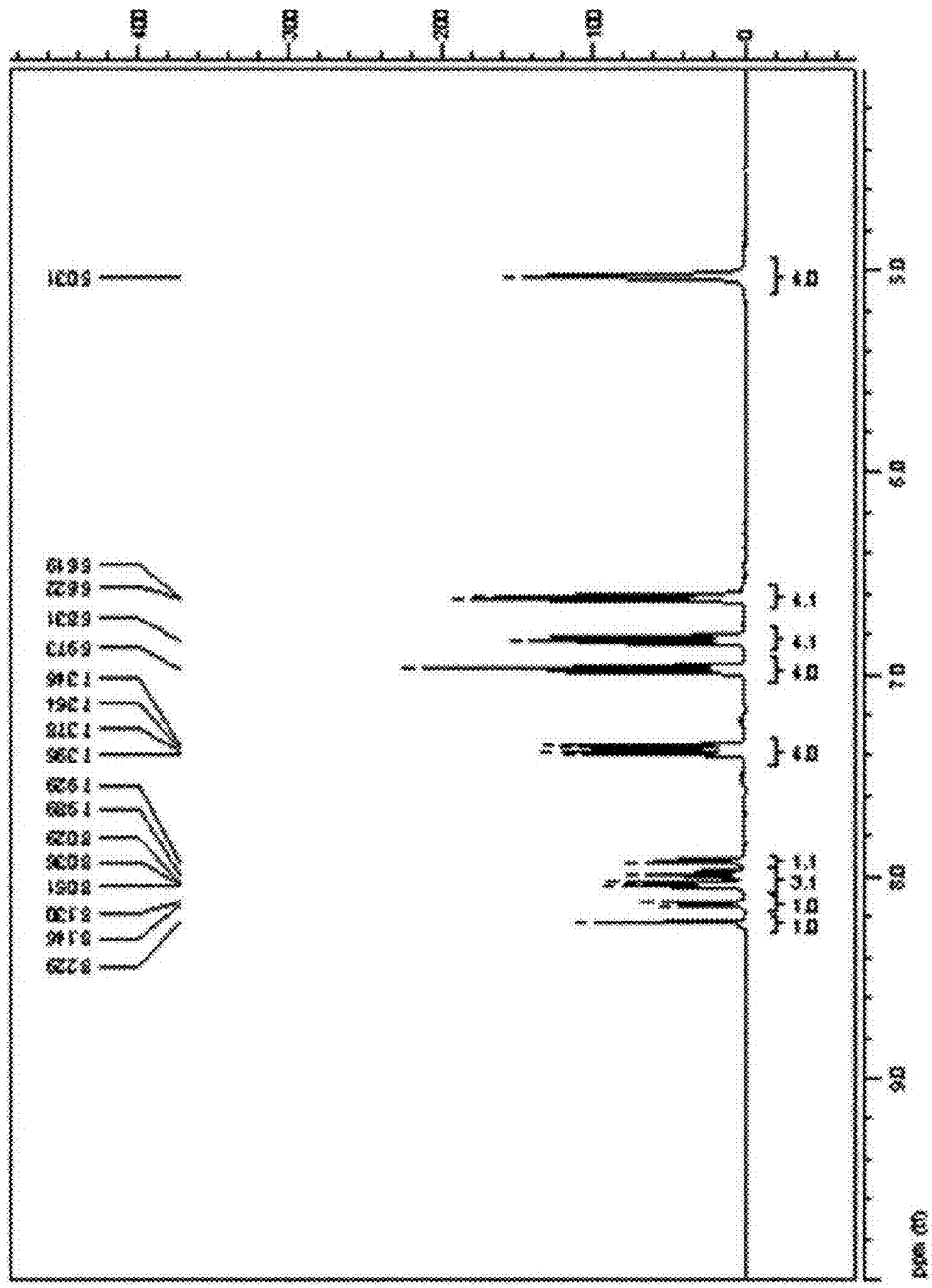
Figure 9:
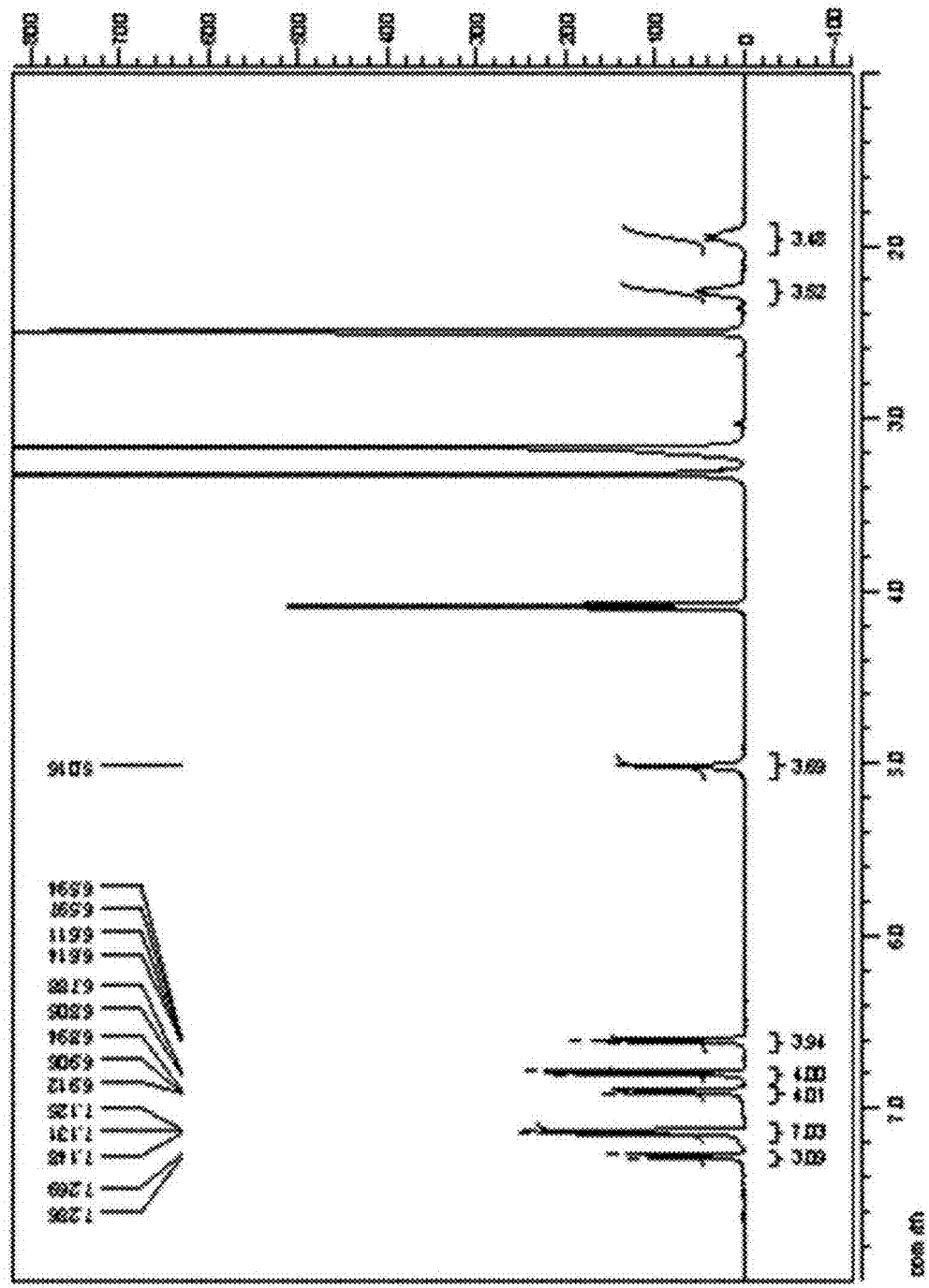

The compound of Formula 18 below was synthesized by dehydration and condensation of a diamine and a dianhydride. 24 g of the compound of Formula VI (4,4'-oxydianiline) in Production Example 3 and 45 g of NMP (N-methylpyrrolidone) were charged into a 3 neck RBF (3 neck round bottom flask) and dissolved by stirring at room temperature. The above solution was cooled with a water bath, and 11.8 g of the compound of Formula 17 below was slowly divided into three times and added thereto together with 45 g of NMP. When all the added compounds were dissolved, 18 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to soxhlet extraction with methanol to remove the residual reactant and dried in a vacuum oven to obtain the compound of Formula 18 in a yield of about 87% by weight. The NMR analysis result of the compound of Formula 18 was shown in FIG. 8.

of Formula 20 in a yield of about 75% by weight. The NMR analysis result of the compound of Formula 20 was shown in FIG. 9.

[Formula 19]

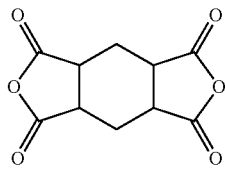

[Formula 17]

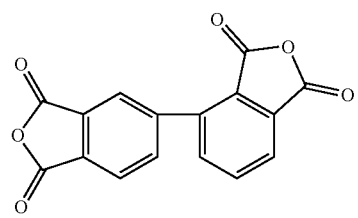

[Formula 18]

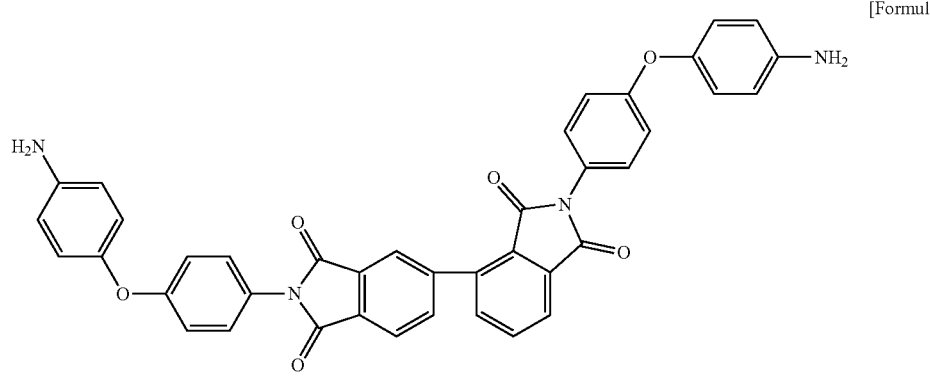

Production Example 9. Synthesis of Compound (CA7)

The compound of Formula 20 below was synthesized by dehydration and condensation of a diamine and a dianhydride. 24 g of the compound of Formula VI (4,4'-oxydianiline) in Production Example 3 and 45 g of NMP (N-methylpyrrolidone) were charged into a 3 neck RBF (3 neck round bottom flask) and dissolved by stirring at room temperature. The above solution was cooled with a water bath, and 9 g of the compound of Formula 19 below was slowly divided into three times and added thereto together with 41 g of NMP. When all the added compounds were dissolved, 18 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to soxhlet extraction with methanol to remove the residual reactant and dried in a vacuum oven to obtain the compound -continued

[Formula 20]

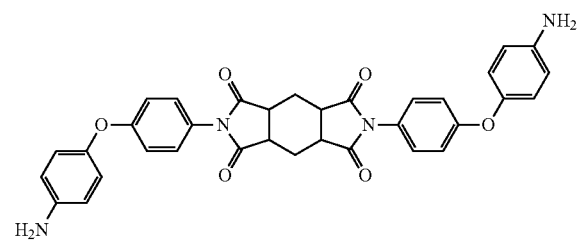

Production Example 10. Synthesis of Compound (CA8)

Figure 10:
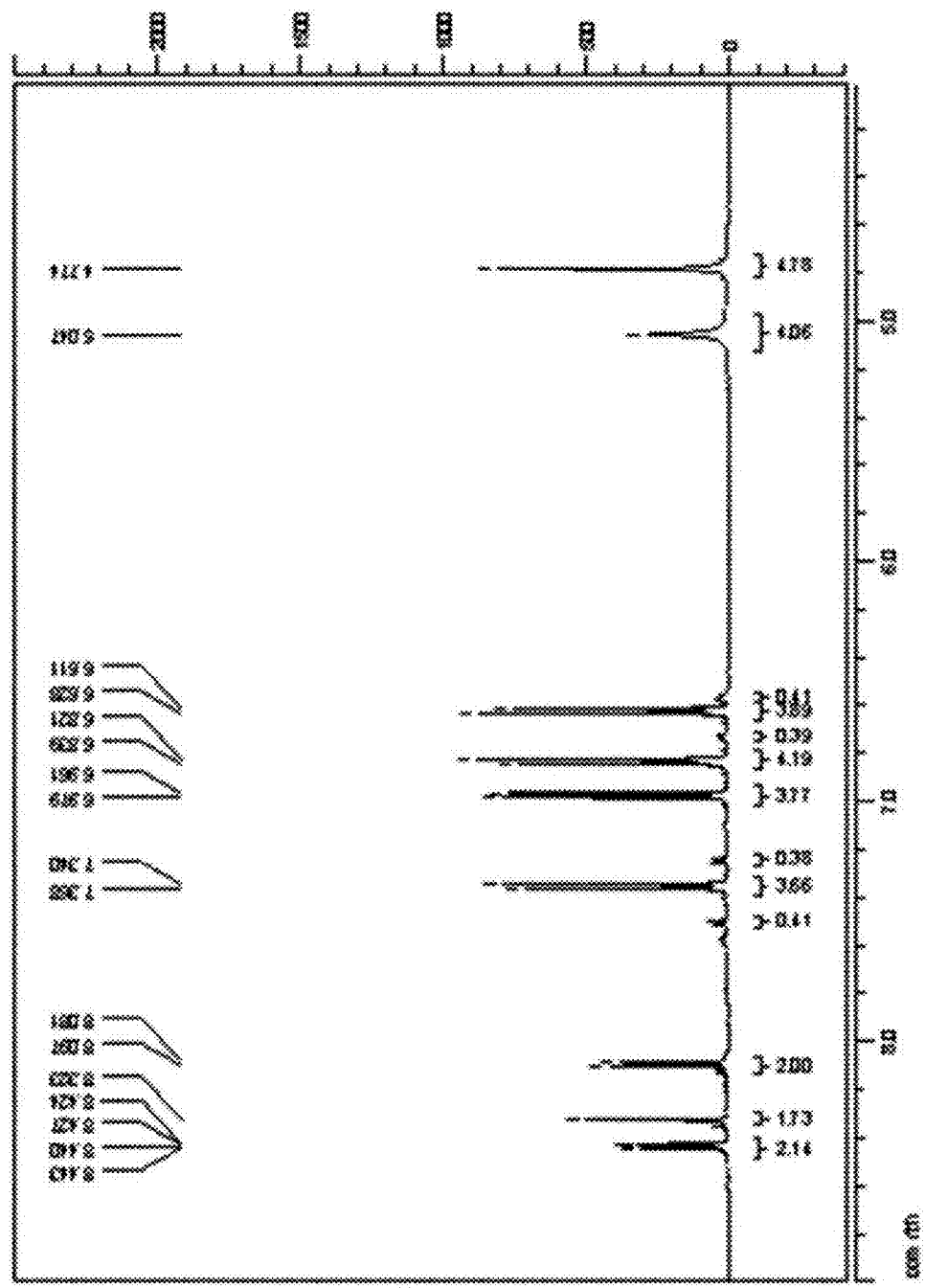

The compound of Formula 22 below was synthesized by dehydration and condensation of a diamine and a dianhydride. 24 g of the compound of Formula VI (4,4'-oxydianiline) in Production Example 3 and 60 g of NMP (N-methylpyrrolidone) were charged into a 3 neck RBF (3 neck round bottom flask) and dissolved by stirring at room temperature. The above solution was cooled with a water bath, and 12.3 g of the compound of Formula 21 below was slowly divided into three times and added thereto together with 60 g of NMP. When all the added compounds were dissolved, 24 g of toluene was added to the reactant for azeotrope. A Dean Stark unit and a reflux condenser were installed, and the Dean Stark unit was charged with toluene added. 4.2 mL of pyridine was added as a catalyst for dehydration and condensation, followed by raising the temperature to 170° C. and stirring for 3 hours. The reactant was further stirred for 2 hours while removing water generated as imide rings were formed, with the Dean Stark unit, and the residual toluene and pyridine were removed. The reaction product was cooled to room temperature, precipitated in methanol and recovered. The recovered precipitate was subjected to soxhlet extraction with methanol to remove the residual reactant and dried in a vacuum oven to obtain the compound of Formula 22 in a yield of about 87% by weight. The NMR analysis result of the compound of Formula 22 was shown in FIG. 10.

pound (CA9) of Production Example 11. While the compound of CA9 is fully decomposed near 330° C., the compounds of CA1 to CA8 have a Td10% of 300° C. or higher, and thus it can be seen that thermal decomposition hardly occurs even in high temperature calcination.

TABLE 1

|  | Td10% | Residue at 800° C. | Td100% |
| --- | --- | --- | --- |
| Production Example 3 (CA1) | 303° C. | 43.3% | — |
| Production Example 4 (CA2) | 356° C. | 48.9% | — |
| Production Example 5 (CA3) | 382° C. | 44.3% | — |
| Production Example 6 (CA4) | 354° C. | 29.1% | — |
| Production Example 7 (CA5) | 319° C. | 45.1% | — |
| Production Example 8 (CA6) | 393° C. | 50.8% | — |
| Production Example 9 (CA7) | 436° C. | 29.1% | — |
| Production Example 10 (CA8) | 390° C. | 41.9% | — |
| Production Example 11 (CA9) | 264° C. | 0% | 331° C. |

[Formula 21]

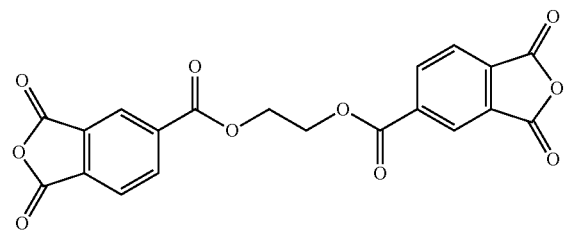

[Formula 22]

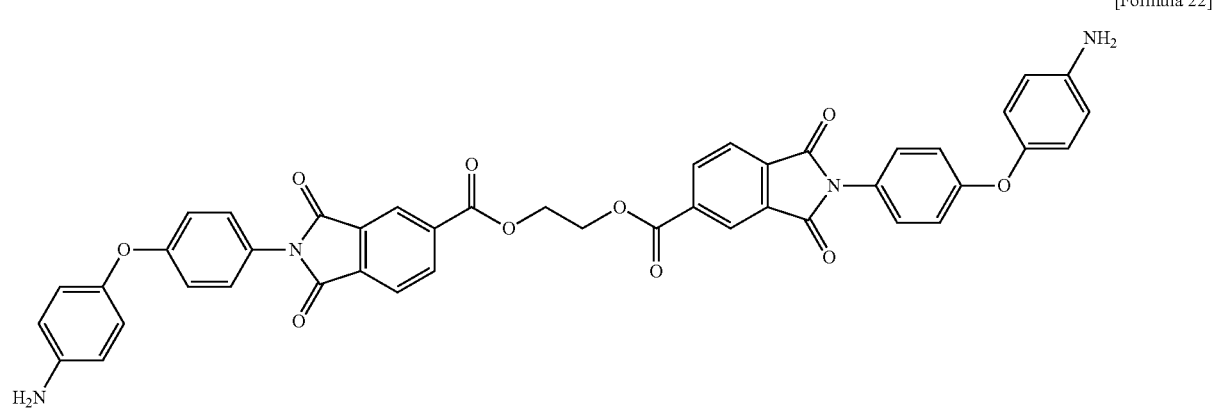

Production Example 11. Synthesis of Compound (CA9)

As the compound of Formula 23 below (CA9), a commercially available product from TCI (Tokyo Chemical Industry Co., Ltd.) was obtained and used without further purification.

[Formula 23]

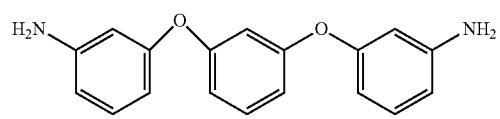

TGA analysis results for the compounds of Production Examples 3 to 11 were summarized and shown in Table 1 below. From Table 1, it can be confirmed that the compounds (CA1 to CA8) of Production Examples 3 to 10 represent heat resistance characteristics superior to the com- Example 1

Figure 11:
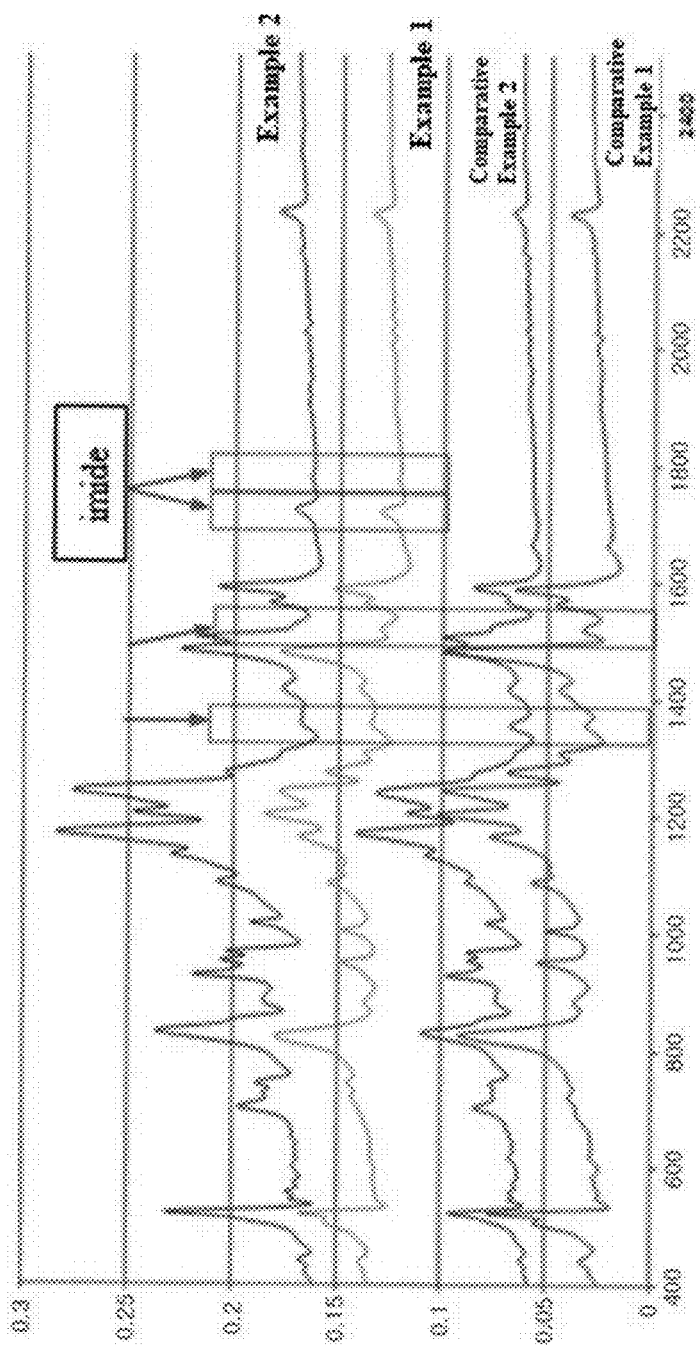
FIG. 11 is the FT-IR analysis results for polymerizable compositions of Examples and Comparative Examples.

About 6 mol % of the compound (CA1) of Production Example 3 relative to the used amount of the compound (PN1) in Production Example 1 was added to the compound (PN1) and mixed well to prepare a polymerizable composition. The results of performing the FT-IR analysis on the composition were shown in FIG. 11. When the polymerizable composition is melted at 240 and stirred for 5 minutes, it is possible to prepare a prepolymer. As shown in FIG. 11, the imide stretching peaks were observed at 1720 cm$^{-1}$ and 1770 cm$^{-1}$ from the FR-IR analysis result and thus it can be confirmed that the polymerizable composition exhibits excellent heat resistance and the like (the graph of Example 1 is the second graph at the top of FIG. 11).

Example 2

About 6 mol % of the compound (CA1) of Production Example 3 relative to the used amount of the compound (PN2) in Production Example 2 was added to the compound (PN2) and mixed well to prepare a polymerizable composition. The results of performing the FT-IR analysis on the composition were shown in FIG. 11. When the polymerizable composition is melted at 240 and stirred for 5 minutes, it is possible to prepare a prepolymer. As shown in FIG. 11, the imide stretching peaks were observed at 1720 $cm^{-1}$ and 1770 $cm^{-1}$ from the FR-IR analysis result and thus it can be confirmed that the polymerizable composition exhibits excellent heat resistance and the like (the graph of Example 2 is the top graph of FIG. 11).

Example 3

A polymerizable composition and a prepolymer were prepared in the same manner as in Example 1, except that the compound (CA2) of Production Example 4 was used instead of the compound (CA1) of Production Example 3. Also, in the case of Example 3, the imide stretching peaks can be observed at 1720 $cm^{-1}$ and 1770 $cm^{-1}$ from the FT-IR analysis.

Example 4

A polymerizable composition and a prepolymer were prepared in the same manner as in Example 1, except that the compound (CA3) of Production Example 5 was used instead of the compound (CA1) of Production Example 3. Also, in the case of Example 4, the imide stretching peaks can be observed at 1720 $cm^{-1}$ and 1770 $cm^{-1}$ from the FT-IR analysis.

Example 5

A polymerizable composition and a prepolymer were prepared in the same manner as in Example 1, except that the compound (CA4) of Production Example 6 was used instead of the compound (CA1) of Production Example 3. Also, in the case of Example 5, the imide stretching peaks can be observed at 1720 $cm^{-1}$ and 1770 $cm^{-1}$ from the FT-IR analysis.

Example 6

A polymerizable composition and a prepolymer were prepared in the same manner as in Example 1, except that the compound (CA5) of Production Example 7 was used instead of the compound (CA1) of Production Example 3. Also, in the case of Example 6, the imide stretching peaks can be observed at 1720 $cm^{-1}$ and 1770 $cm^{-1}$ from the FT-IR analysis.

Example 7

A polymerizable composition and a prepolymer were prepared in the same manner as in Example 1, except that the compound (CA6) of Production Example 8 was used instead of the compound (CA1) of Production Example 3. Also, in the case of Example 7, the imide stretching peaks can be observed at 1720 $cm^{-1}$ and 1770 $cm^{-1}$ from the FT-IR analysis.

Example 8

A polymerizable composition and a prepolymer were prepared in the same manner as in Example 1, except that the compound (CA7) of Production Example 9 was used instead of the compound (CA1) of Production Example 3. Also, in the case of Example 8, the imide stretching peaks can be observed at 1720 $cm^{-1}$ and 1770 $cm^{-1}$ from the FT-IR analysis.

Example 10

A polymerizable composition and a prepolymer were prepared in the same manner as in Example 1, except that the compound (CA8) of Production Example 10 was used instead of the compound (CA1) of Production Example 3. Also, in the case of Example 10, the imide stretching peaks can be observed at 1720 $cm^{-1}$ and 1770 $cm^{-1}$ from the FT-IR analysis.

Comparative Example 1

About 6 mol % of the compound (CA9) of Production Example 11 relative to the used amount of the compound (PN1) in Production Example 1 was added to the compound (PN1) and mixed well to prepare a polymerizable composition. The results of performing the FT-IR analysis on the composition were shown in FIG. 11. When the polymerizable composition is melted at 240 and stirred for 5 minutes, it is possible to prepare a prepolymer. As shown in FIG. 11, no imide stretching peak was observed from the FR-IR analysis result and thus it can be confirmed that the polymerizable composition has poor physical properties such as heat resistance as compared with Examples (the graph of Comparative Example 1 is the fourth graph at the top of FIG. 11).

Comparative Example 2

About 6 mol % of the compound (CA9) of Production Example 11 relative to the used amount of the compound (PN2) in Production Example 2 was added to the compound (PN2) and mixed well to prepare a polymerizable composition. The results of performing the FT-IR analysis on the composition were shown in FIG. 11. When the polymerizable composition is melted at 240 and stirred for 5 minutes, it is possible to prepare a prepolymer. As shown in FIG. 11, no imide stretching peak was observed from the FR-IR analysis result and thus it can be confirmed that the polymerizable composition has poor physical properties such as heat resistance as compared with Examples (the graph of Comparative Example 2 is the third graph at the top of FIG. 11).

The invention claimed is:
1. A polymerizable composition consisting of a phthalonitrile compound, a compound of Formula 1 below, and optionally an additive selected from a metal material, a ceramic material, glass, a metal oxide, a metal nitride or a carbon-based material:

[Formula 1]

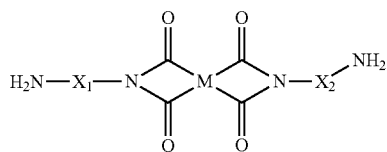

wherein M is a tetravalent radical, and $X_1$ and $X_2$ are each independently an alkylene group, an alkylidene group or an aromatic divalent radical.

2. The polymerizable composition according to claim 1, wherein the tetravalent radical is a tetravalent radical derived from an aliphatic, alicyclic or aromatic compound.

3. The polymerizable composition according to claim 1, wherein the tetravalent radical is a tetravalent radical derived from an alkane, alkene or alkyne, or a tetravalent radical derived from a compound represented by any one of Formulas 2 to 7 below:

[Formula 2]

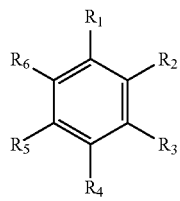

wherein $R_1$ to $R_6$ are each independently hydrogen, an alkyl group, an alkoxy group or an aryl group;

[Formula 3]

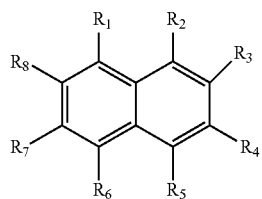

wherein $R_1$ to $R_8$ are each independently hydrogen, an alkyl group, an alkoxy group or an aryl group;

[Formula 4]

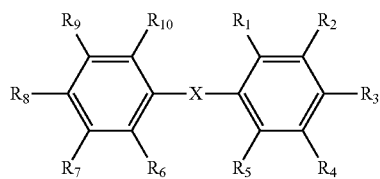

wherein $R_1$ to $R_{10}$ are each independently hydrogen, an alkyl group, an alkoxy group or an aryl group, and X is a single bond, an alkylene group, an alkylidene group, an oxygen atom, a sulfur atom, a carbonyl group, $-A_1-O-C(=O)-A_2-$, $-A_1-C(=O)-O-A_2-$, $-S(=O)-$, or $-S(=O)_2-$, wherein $A_1$ and $A_2$ are each independently a single bond or an alkylene group;

[Formula 5]

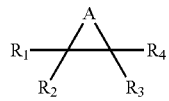

wherein $R_1$ to $R_4$ are each independently hydrogen, an alkyl group or an alkoxy group, and A is an alkylene group or an alkenylene group, wherein two of $R_1$ to $R_4$ are linked to each other to form an alkylene group, and the alkylene group or the alkenylene group of A contains one or more oxygen atoms as a hetero atom;

[Formula 6]

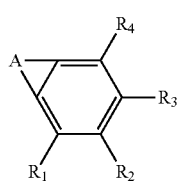

wherein $R_1$ to $R_4$ are each independently hydrogen, an alkyl group or an alkoxy group, and A is an alkylene group;

[Formula 7]

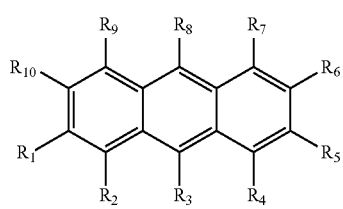

wherein $R_1$ to $R_{10}$ are each independently hydrogen, an alkyl group or an alkoxy group.

4. The polymerizable composition of claim 1, wherein each of $X_1$ and $X_2$ is an aromatic divalent radical.

5. The polymerizable composition according to claim 4, wherein the aromatic divalent radical is a divalent radical derived from an aromatic compound having 6 to 40 carbon atoms.

6. The polymerizable composition according to claim 1, wherein each of $X_1$ and $X_2$ is a divalent radical derived from a compound represented by any one of Formulas 8 to 10 below:

[Formula 8]

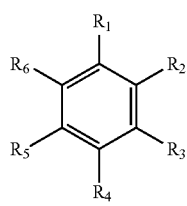

wherein $R_1$ to $R_6$ are each independently hydrogen, an alkyl group, an alkoxy group, an aryl group, a hydroxy group or a carboxyl group;

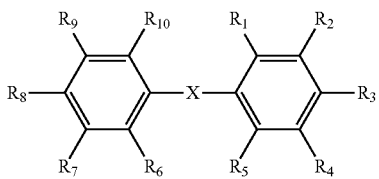

[Formula 9]

wherein $R_1$ to $R_{10}$ are each independently hydrogen, an alkyl group, an alkoxy group, a hydroxy group, a carboxyl group or an aryl group, and X is a single bond, an alkylene group, an alkylidene group, an oxygen atom, a sulfur atom, a carbonyl group, -$A_1$-O—C(=O)-$A_2$-, -$A_1$-C(=O)—O-$A_2$-, —$NR_{11}$—, —S(=O)— or —S(=O)$_2$—, wherein $R_{11}$ is hydrogen, an alkyl group, an alkoxy group or an aryl group, and $A_1$ and $A_2$ are each independently a single bond or an alkylene group;

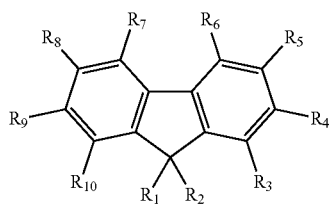

[Formula 10]

wherein $R_1$ to $R_{10}$ are each independently hydrogen, an alkyl group, an alkoxy group, a hydroxy group, a carboxyl group or an aryl group.

7. The polymerizable composition of claim 1, wherein the compound of Formula 1 has a 10 wt % decomposition temperature of 300° C. or higher.

8. The polymerizable composition according to claim 1, which has a processing temperature (Tp) in a range of 150° C. to 350° C.

9. The polymerizable composition according to claim 1, wherein an amount of the compound of Formula 1 is from about 0.02 moles to about 1.5 moles per mole of the phthalonitrile compound.

10. A prepolymer which is formed by a reaction of the polymerizable composition of claim 1.

11. The prepolymer according to claim 10, which has a melt viscosity in a range of 100 cP to 10,000 cP at a temperature in a range of 150° C. to 250° C.

12. The prepolymer according to claim 10, wherein the reaction is processed at a processing temperature (Tp) in a range of 150° C. to 350° C.

13. A phthalonitrile resin which is a polymer of the polymerizable composition of claim 1.

14. A composite comprising the phthalonitrile resin of claim 13 and a filler.

15. The composite according to claim 14, wherein the filler is fibrous materials or carbon nanomaterials.

16. A process for preparing a composite comprising: curing the polymerizable composition of claim 1.

\* \* \* \* \*